United States Patent
Young et al.

(10) Patent No.: US 7,598,354 B2
(45) Date of Patent: Oct. 6, 2009

(54) CAMPYLOBACTER GLYCANS AND GLYCOPEPTIDES

(75) Inventors: Noel M. Young, Ottawa (CA); Jean-Robert Brisson, Ottawa (CA); John Francis Kelly, Ottawa (CA); David C. Watson, Ottawa (CA); Harold C. Jarrell, Ottawa (CA); Christine M. Szymanski, Ottawa (CA)

(73) Assignee: National Research Council of Canada, Ottawa, Ontario (CA)

( * ) Notice: Subject to any disclaimer, the term of this patent is extended or adjusted under 35 U.S.C. 154(b) by 155 days.

(21) Appl. No.: 10/523,459

(22) PCT Filed: Jul. 30, 2003

(86) PCT No.: PCT/CA03/01156

§ 371 (c)(1),
(2), (4) Date: Jan. 31, 2005

(87) PCT Pub. No.: WO2004/013151

PCT Pub. Date: Feb. 12, 2004

(65) Prior Publication Data

US 2006/0165728 A1 Jul. 27, 2006

Related U.S. Application Data

(60) Provisional application No. 60/399,735, filed on Aug. 1, 2002.

(51) Int. Cl.
*A61K 39/02* (2006.01)
*C08B 37/00* (2006.01)

(52) U.S. Cl. .................... 530/395; 536/53; 424/197.11; 435/34

(58) Field of Classification Search ........................ None
See application file for complete search history.

(56) References Cited

U.S. PATENT DOCUMENTS 4,925,796 A * 5/1990 Bergh et al. .................... 435/97

(Continued)

FOREIGN PATENT DOCUMENTS

| EP | 0779932 | * | 8/2000 |
| WO | 92/08485 | * | 5/1992 |
| WO | 00/51635 | * | 9/2000 |

OTHER PUBLICATIONS

Young, N. Martin et al, The Journal of Biological Chemistry, vol. 277, (26) Nov. 8, pp. 42530-42539, 2002.*

(Continued)

*Primary Examiner*—Robert B Mondesi
*Assistant Examiner*—Ginny Portner
(74) *Attorney, Agent, or Firm*—Townsend and Townsend and Crew, LLP

(57) ABSTRACT

Multiple strains and species of Campylobacter share a common glycan moiety which is present in a plurality of surface-exposed glycoproteins. This glycan has the formula: GalNAc-a1, 4-GalNAc-a1,4-[Glc-β1,3]GalNAc-a1,4-GalNAc-a1,4-GalNAc-a1,3-Bac, wherein Bac is 2, 4-diacetamido-2,4,6-trideoxy-D-glucopyranose. This glycan and immunologically active fragments of it have use as vaccines against campylobacter infection in humans and animals. As well, antibodies which specifically bind these compounds may be provided. Such antibodies and vaccines may be used to prevent or neutralize campylobacter infections in livestock thereby preventing this pathogen from entering the human food chain. The glycan may be linked to one or more amino acids to form a glycopeptide. As well, a method for determining the glycan structure of an intact glycoprotein consists of subjecting a sample to high resolution magic angle spinning nuclear magnetic resonance (HR-MAS-NMR) spectroscopy.

18 Claims, 12 Drawing Sheets

U.S. PATENT DOCUMENTS

| | | | | |
|---|---|---|---|---|
| 5,200,344 | A | * | 4/1993 | Blaser et al. ............... 435/7.32 |
| 5,470,958 | A | * | 11/1995 | Blaser et al. ............. 530/389.5 |
| 5,840,547 | A | * | 11/1998 | Rosenberg et al. ............ 516/70 |
| 6,512,014 | B2 | * | 1/2003 | Gutnick et al. ................ 516/70 |
| 6,676,946 | B2 | * | 1/2004 | Bay et al. .............. 424/196.11 |
| 2002/0143071 | A1 | * | 10/2002 | Gutnick et al. ................ 516/70 |
| 2003/0232401 | A1 | * | 12/2003 | Pugia et al. ................ 435/7.32 |
| 2004/0137557 | A1 | * | 7/2004 | DeFrees et al. ............ 435/68.1 |
| 2004/0265340 | A1 | * | 12/2004 | Kaplan et al. ............ 424/234.1 |
| 2007/0048854 | A1 | * | 3/2007 | Gilbert et al. ............... 435/193 |
| 2007/0065461 | A1 | * | 3/2007 | Guerry et al. ............ 424/234.1 |

OTHER PUBLICATIONS

Szymanski, Christine M. et al, Molecular Microbiology, 1999, vol. 32(5) pp. 1022-1030, Evidence for a system of general protein glycosylation in Campylobacter jejuni.*

Linton, Dennis et al, Molecular Microbiology, Jan. 2002, vol. 43(2), pp. 497-508, Identification of N-acetylgalactosamine-containing glycoproteins PEB3 and CgpA in Campylobacter jejuni.*

Messner, Paul et al, Journal of Bacteriology, May 1990, vol. 172(5), apges 2576-2583, Characterization of the surface layer glycoprotein of Clostridium symbiosum HB25.*

Schaffer, Christina et al, Eur. J. Biochem., vol. 268, pp. 857-864, 2001, Purification and structure elucidation of the N-acetylbacillosamine-containing polysaccharide from Bacillus licheniformis ATCC 9945.*

Young, N. Martin et al, The Journal of Biological Chemistry, vol. 277(45) Nov. 8, 2002, pp. 42530-42539.*

Bacon, David J. et al, A phase variable capsule is involved in virulence of Campylobacter jejuni 81-176, Molecular Microbiology, 2001, pp. 769-777, vol. 40(3).*

Thibault, Pierre et al, The Journal of Biological Chemistry, vol. 276(37), Sep. 14, 2001, pp. 34862-34870, Identification of the Carbohydrate moieties and glycosylation motifs in Campylobacter jejuni flagellin.*

Benz, Inga et al, Molecular Microbiology, vol. 45(2), pp. 267-276, 2002, Never say never again: protein glycosylation in pathogenic bacteria.*

Dorrell, Nick et al, Genome Res. 2001, vol. 11, pp. 1706-1715, Whole Genome Comparison of Campylobacter jejuni Human isolates using a low-cost microarray reveals extensive genetic diversity.*

Bowes, Tyrone et al, Infection and Immunity, vol. 70(9), pp. 5008-5018, Sep. 2002, Tolerance of Self Gangliosides is the major factor restricting the antibody response to lipopolysaccharide core oligosaccharides in Campylobacter jejuni strains associated with Guillain-Barre Syndrome.*

Rangarajan, Erumbi S. et al, Protein Science, 2007, vol. 16, pp. 990-995, Structural context for protein N-glycosylation in bacteria, the structure of PEB3, an adhesin from Campylobacter jejuni.*

Ang, CW et al, Structure of Campylobacter jejuni Lipopolysaccharides Determines Antiganglioside Specificity and Clinical features of Guillain-Barre and Miller Fisher Patients, Infection and Immunity, Mar. 2002, pp. 1202-1208, vol. 70-(3).*

Oldfield, Neil J. et al, Journal of Bacteriology, Apr. 2002, pp. 2100-2107, vol. 184(8), Characterization of the Campylobacter jejuni Heptosyltransferase II gene, waaF, provides genetic evidence that extracellular polysaccharide is Lipid A Core independent.*

Karlyshev, Andrey V et al, Journal of Clinical Microbiology, Jan. 2001, pp. 279-284, vol. 39(1), Detection and Initial Characterization of Novel Capsular Polysaccharide among diverse Campylobacter jejuni strains using Alcian Blue dye.*

Pei, Zhiheng et al, Pathogenesis of Campylobacter fetus Infections, J. Clin. Invest., Vol. 85, Apr. 1990, pp. 1036-1143.*

Pei, Zhiheng et al, The Journal of Biological Chemistry, Sep. 5, 1991, p. 16363-16369, Identification, Purification and Characterization of Major Antigenic Proteins of Campylobacter jejuni.*

Pei, Zhiheng et al, Journal of Clinical Investigation, vol. 85, pp. 1036-1043, Apr. 1990.*

Rangarajan, Erumbi S et al, Protein Science, 2007, vol. 16, pp. 990-995, Structural context for protein N-glycosylation in bacteria: The structure of PEB3, an adhesin from Campylobacter jejuni.*

Szymanski, Christine M. et al, Moleuclar Microbiology, 1999, vol. 32(5), pp. 1022-1030, Evidence for a system of general protein glycosylation in Campylobacter jejuni.*

Pei, Z et al, The Journal of Biological Chemistry, pp. 16363 16369.*

Rangarajan, Erumbi S et al, Protein Science, 2007, vol. 16, pp. 990-995, Structural context for protein N-glycosylation in bacteria: The structure of PEB3, an adhesin from Campylobacter jejuni.*

Kieliszewski, Marcia Jane, Phytochemistry, vol. 57, (2001) pp. 319-323, The latest hype on Hyp-)-glycosylation codes.*

Linton, D et al, Current Opinion Microbiology, Feb. 2001, vol. 4(1), pp. 35-40, Deciphering Campylobacter jejuni cell surface interactions from the genome sequence.*

Schäffer, C., Graninger, M., and Messner, P. (2001) Proteomics. 1, 248-261.

Moens, S. and Vanderleyden, J. (1997) Arch. Microbiol. 168, 169-175.

Szymanski, C.M., Yao, R., Ewing, C.P., Trust, T.J., and Guerry, P. (1999) Mol. Microbiol. 32(5), 1022-1030.

Szymanski, C.M., Burr, D.H., and Guerry, P. (2002) Infect. Immun. 70, 2242-2244.

Thibault, P., Logan, S.M., Kelly, J.F., Brisson, J.R., Ewing, C.P., Trust, T.J., and Guerry, P. (2001) J. Biol. Chem. 276, 34862-34870.

Parkhill, J., Wren, B.W., Mungall, K., Ketley, J.M., Churcher, C., Basham, D., Chillingworth, T., Davies, R.M., Feltwell, T, Holroyd, S., Jagels, K., Karlyshev, A.V., Moule, S., Pallen, M.J., Penn, C.W., Quail, M.A., Rajandream, M.A., Rutherford, K.M., van Vliet, A.H., Whitehead, S., and Barrel, B.G. (2000) Nature 403, 665-668.

Pei, Z.H., Ellison, R.T., III, and Blaser, M.J. (1991) J. Biol. Chem. 266(25), 16363-16369.

Linton, D., Allan, E., Karlyshev, A.V., Cronshaw, A.D., And Wren, B.W. (2002) Mol. Microbiol. 43(2), 497-508.

Muldoon, J., Savage, A., Ferris, J.A., Shashkov, A., Moran, A.P. (2001) Int. J. Med. Microbiol. 291 Suppl 31, 81.

Young, N.M., Brisson, J.R., Kelly, J., Watson, D.C., Tessier, L., Lanthier, P.H., Jarrell, H.C., Cadotte, N., St Michael, F., Aberg, E., and Szymanski, C.M. (2002) J. Biol. Chem. 277(45), 42530-42539.

Hermansson, K., Perry, M.B., Altman, E., Brisson, J.R., and Garcia, M.M. (1993) Eur. J. Biochem. 212, 801-809.

Molinaro, A., Evidente, A., Sante, I.N., Lanzetta, R., Lo, C.P., Mancino, A., and Parrilli, M. (2002) Carbohydr. Res. 337, 467-471.

Schäffer, C., Scherf, T., Christian, R., Kosma, P., Zayni, S., Messner, P., and Sharon, N. (2001) Eur. J. Biochem. 268, 857-864.

Patel, T., Bruce, J., Merry, A., Bigge, C., Wormald, M., Jaques, A., and Parekh, R. (1993) Biochemistry 32, 679-693.

* cited by examiner

SEQUENCE LISTING

```
<160> NUMBER OF SEQ ID NOS: 10

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:
      Campylobacter jejuni major antigenic peptide PEB3 tryptic
      glycopeptide
<220> FEATURE:
<221> NAME/KEY: MOD_RES
<222> LOCATION: (3)
<223> OTHER INFORMATION: Xaa = Asn modified by N-linked oligosaccharide

<400> SEQUENCE: 1

Asp Phe Xaa Val Ser Lys
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:
      Campylobacter jejuni major antigenic peptide PEB3 tryptic
      peptide

<400> SEQUENCE: 2

Asp Phe Asn Val Ser Lys
1               5

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:PCR
      amplification primer Cj1121cF
```

-continued

```
<400> SEQUENCE: 3
actcactatt gccattaaga taagc                                          25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:PCR
      amplification primer Cj1126cR

<400> SEQUENCE: 4
aaaaccctta tttagttttg tttgc                                          25

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence:
      Campylobacter jejuni Cj1670c glycopeptide

<400> SEQUENCE: 5

Thr Asp Gln Asn Ile Thr Leu Val Ala Pro Pro Glu Phe Gln Lys Glu
 1               5                  10                  15

Glu Val Lys

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence:
      Campylobacter jejuni Cj1670c glycopeptide

<400> SEQUENCE: 6

Val Leu Asp Val Ser Val Thr Ile Pro Glu Lys Asn Ser Ser Lys
 1               5                  10                  15

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence:
      Campylobacter jejuni Cj1670c glycopeptide

<400> SEQUENCE: 7

Gln Glu Ser Asn Ser Thr Ala Asn Val Glu Ile Pro Leu Gln Val Ala
 1               5                  10                  15

Lys

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence:
      Campylobacter jejuni Cj0114 glycopeptide

<400> SEQUENCE: 8

Leu Ser Gln Val Glu Glu Asn Asn Gln Asn Ile Glu Asn Asn Phe Thr
 1               5                  10                  15

Ser Glu Ile Gln Lys
            20
```

-continued

```
<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence:
      Campylobacter jejuni Cj0200c glycopeptide

<400> SEQUENCE: 9

Asp Ser Leu Lys Leu Glu Gly Thr Ile Ala Gln Ile Tyr Asp Asn Asn
 1               5                  10                  15

Lys

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:sequencing
      primer ckanB

<400> SEQUENCE: 10
cctgggtttc aagcattag                                             19
```

CAMPYLOBACTER GLYCANS AND GLYCOPEPTIDES

FIELD OF THE INVENTION

The invention is in the field of biologically active glycoproteins and glycan moieties of glyocoproteins as well as vaccines, antibodies and antibody fragments useful for combating *campylobacter* bacteria.

BACKGROUND OF THE INVENTION

*Campylobacter* is a significant food borne pathogen in livestock products, including poultry. It is thus desirable to provide strategies for combating its deleterious effects in humans. Elimination of these pathogens from livestock can serve as a means to reduce the incidence of infection in humans and reduce disease in farm animals that are affected. Glycosylated proteins and in particular certain glycan moieties of these compounds represent viable targets for immunologic strategies to reduce or eliminate the presence of these organisms in livestock, in order to reduce the risk of human contamination from eating or handling animal products as well as contamination by fecal shedding of bacteria from livestock manure. Glycoproteins and their fragments such as glycan moieties may also provide a basis for vaccines and antibody preparation which target *campylobacter* infections.

It is also desirable to provide research tools having general application for studying protein glycosylation. Glycosylation of proteins was once considered to be specifically a eukaryotic phenomenon, but it is now clear that it is widespread in both the Archaea and Eubacteria domains (1,2). Glycosidic linkages of both the N- and O- types have been identified in a diverse group of prokaryotic organisms with a preponderance of N-linked sugars apparent in the Archaea while linkage units of the O-type predominate in glycoproteins identified thus far in the Eubacteria (1,2). In addition, bacterial N- and O- linkages are formed with a wider range of sugars than those observed in eukaryotic glycoproteins.

The present inventors have discovered that certain glycopeptides and gylcan moieties form an effective basis for vaccines and antibodies against multiple strains of *campylobacter* bacteria, by virtue of their ubiquitous presence on the surface of these bacteria in an invariant (or nearly invariant) form across multiple strains and species. This glycan is also present as a component of a plurality of surface glycoproteins of *campylobacter* thus enhancing its value as an immunologic target.

Recently a gene locus was identified in the enteric pathogen *Campylobacter jejuni*, which appears to be involved in the glycosylation of multiple proteins. This provided the first evidence of a pathway for wide-spread protein glycosylation in a gram-negative bacterium (3). Mutagenesis of genes within this locus, termed pgl (for protein glycosylation), resulted in loss of immunogenicity in multiple proteins. The glycan moieties of these proteins were also shown to be recognized by antisera from experimentally infected human volunteers (3). Removal of the glycan moieties by pgl mutation resulted in decreased adherence and invasion in vitro and loss of mouse colonization in vivo (4), suggesting that protein glycosylation influences the virulence properties of this organism.

The present inventors have identified and characterized post-translational modifications of proteins in *C. jejuni* strain NCTC 11168, the strain for which the whole genome sequence has been described by Parkhill et al. (6). Among the proteins giving rise to multiple spots on 2D gels was PEB3, or Cj0289c, a major antigenic protein of *C. jejuni* first described by Pei et al. (7). When purified and analysed by 1D SDS-PAGE, it revealed two bands with a mass difference of ~1500 Da, both of which had N-terminal sequences corresponding to authentic PEB3. Concurrent with our observations on PEB3, Linton et al. (8) identified two putative glycoproteins from *C. jejuni* by use of the GalNAc-specific lectin, soybean agglutinin, one of which was PEB3, and the other a putative periplasmic protein Cj1670c, which they named CgpA. The authors also observed a number of other putative glycoproteins, based upon their ability to bind to the lectin, but these were not identified. Furthermore, protein binding to the lectin was also affected by mutagenesis of genes in the pgl locus. In addition, we have shown that mutation of a gene pglB, whose homology to the STT3 subunit of the N-linked oligosaccharyltransferase of *Saccharomyces cerevisae* suggested a role in glycoprotein biosynthesis (3,9), specifically affects the glycosylation of the identified glycoproteins.

Moreover, carbohydrates are implicated in a variety of functions in all domains of life. While in general there is high degree of variance of glycoproteins and their glycan moieties in antigenic surface glycans between bacterial strains and related species, this is not always the case and such exceptions present suitable excellent candidates for antibody or vaccine-based strategies for eliminating bacteria. In particular, one such carbohydrate is the glycan moiety of *campylobacter* glycoproteins. Our recent efforts to characterize the glycome of the important foodborne pathogen *Campylobacter jejuni*, has led to the elucidation of all surface glycan structures, namely, lipooligosaccharide (LOS), capsular polysaccharide (CPS), N-linked glycans, and O-linked glycans (5, 12-15)

It has been shown by the present inventors that the heptasaccharide, which is described in this specification, is common to at least several *Campylobacter* species and numerous strains including species that are important as human and veterinary pathogens, and is a component of multiple glycoproteins including Cj nos. 0114, 0200c, 0289c, 0367c and others. This glycan moiety is also strongly immunogenic and as such this glycan (and related fragments and glycopeptides) is a good candidate for use as a vaccine for active immunization against multiple strains and species of campylobacter and as the basis for antibodies or antibody fragments suitable for targeting of *campylobacter* in a human or in livestock.

As used herein "livestock" includes mammals and poultry.

SUMMARY OF THE INVENTION

It is an object of the invention to provide a glycan which may exist either in isolation or linked to an oligopeptide, an amino acid and/or an immunogenic conjugate.

In accordance with one aspect, the invention provides a compound comprising a heptasaccharide of formula I: GalNAc-a1,4-GalNAc-a1,4-[Glc-β1,3]GalNAc-a1,4-GalNAc-a1,4-GalNAc-a1,3-Bac, wherein Bac is 2,4-diacetamido-2,4,6-trideoxy-D-glucopyranose. Formula I also includes immunologically active fragments of the compound described above. By "immunologically active" is meant that such fragment may comprise the active component of a vaccine against *campylobacter*, or that antibodies or antibody fragments may be provided which specifically bind to such a compound and to neutralize *campylobacter* in an organism in which the same has been administered. These glycans may be provided in isolated form or linked to an oligopeptide or amino acid to form a novel glycopeptide. The amino acid may comprise asparagine to form an N-linked glycopeptide. These glycans or glycopeptides may be derived from or isolated and purified from a gram negative bacterium. This glycoprotein glycan moiety can also provide the basis for therapeutic preparations and methods as discussed below.

In accordance with yet another aspect, the invention provides a method of detecting a glycan moiety of a bacterial glycoprotein, the method comprising subjecting said sample to high resolution magic angle spinning nuclear magnetic resonance (HR-MAS NMR) spectroscopy. This method allows for the detection of the glycan moiety directly form its source without the need of purifying the protein.

In accordance with a further aspect, the invention provides a pharmaceutical composition which comprises a heptasaccharide of formula I and a physiologically acceptable carrier. Preferably, the pharmaceutical compositions may further comprise an immunogenic conjugate bound to the glycan or glycopeptide or fragment thereof and/or an immunostimulant. Such pharmaceutical compositions are useful as vaccines for immunizing a human or an animal against diseases caused by *campylobacter* pathogens. Such diseases are for example gastro-intestinal infections, Guillain Barré GBS and Miller Fisher syndromes, arthritis and bacteremia. Such vaccines may be administered via one or more injections or by another medically acceptable method.

In accordance with another aspect, the invention provides an antibody or an antigen-binding antibody fragment that interacts and specifically binds with the glycan moiety of Formula I. Such antibodies or fragments may neutralize one or more *Campylobacter* species when administered to an animal or human recipient. Such antibodies can be obtained by various known methods including being isolated from the serum of an animal that has been previously immunized with a heptasaccharide or a glycopeptide as described above or preparing murine monoclonal antibodies directed against such compounds. Another means is via recombinant DNA techniques, for example by obtaining such an antibody or antibody fragment by cloning a library set of domain antibody ("dAb") genes previously isolated from a *camelid*, and then expressed in a bacteriophage library, panning for and then expressing in a bacteriophage a sequence dAbs having an affinity for the heptasaccharide, glycopeptide or fragment thereof. A preferred camelid is selected from *Camelus bactriamus, Camelus dromaderius, Lama pPaccos, Lama ggGlama* and *Lama v*Alternatively, another method could involve screening bacteriophage libraries of single-chain antibody fragments (scFv)*Vicugna*. The invention also provides a pharmaceutical composition comprising the antibody or its antigen-binding fragment as defined above, and a physiologically acceptable carrier. Such pharmaceutical composition can be used as a therapeutic agent in an animal or a human.

Suitable antibody fragments include Fab fragments (although it will be noted that since *Camelid* species produce a unique type of antibody which does not contain light chains, conventional terminology such as "Fab" may be modified) including fragments which are prepared in isolation by the above techniques or by other conventional techmiques and not directly derived from a whole antibody.

In accordance with yet another aspect, the invention provides a method of reducing the presence of *campylobacter* bacteria in livestock. The method comprises administering to livestock the antibody or antigen-binding antibody fragment that interacts and binds with the glycan moiety of Formula I. Such antibody when administered in sufficient quantity neutralizes all or substantially all pathogenic *campylobacter* organisms from the animal's system or prevents colonization by the bacteria thereby preventing the animal from infecting humans, either by eating or handling an animal product or via contamination from animal waste. The administration may consist of feeding the livestock, preferably poultry, with feed or water containing the antibody or antigen-binding fragment. Eliminating the pathogens or reducing their presence in livestock constitutes a way of preventing the pathogens from reaching humans who are therefore prevented from diseases caused by these pathogens. Thus, the invention also provides for a method of preventing *campylobacter* infections caused by *campylobacter* pathogens in a human, the method comprising removing the pathogens from livestock by delivering to the livestock the antibody or antigen-binding fragment thereof as defined above.

The antibodies or antibody fragments may be either added to animal feed or water or alternatively may be present as a result of a genetic modification of an animal feed plant which permits such a plant to express the antibody or antibody fragment.

In accordance with still another aspect, the invention provides a method of treating a disease caused by *campylobacter* pathogens in a human or an animal, the method comprising administering the antibody or antigen-binding fragment thereof as defined above to the human. The antibody or its antigen-binding fragment can be used in the preparation of a medicament for treating an animal or a human for a disease caused by *campylobacter* pathogens.

In accordance with another aspect, the invention provides for method of preventing ground water contamination of *campylobacter* pathogens which arises as a result of fecal shedding of the bacteria by livestock followed by entry of the fecal matter into a water supply. The method comprises eliminating or reducing the presence of the pathogens from livestock by administering to the livestock the antibody or antigen-binding fragment thereof as defined above. This also constitutes a way of preventing the pathogens from reaching humans, therefore preventing them from diseases caused by these pathogens.

The antibodies and antibody fragments of the present invention may also be used as a diagnostic tool to detect the presence of *campylobacter* in humans and animals, as well as in samples drawn from the environment such as water or manure samples.

DETAILED DESCRIPTION OF THE INVENTION

Figure 1:
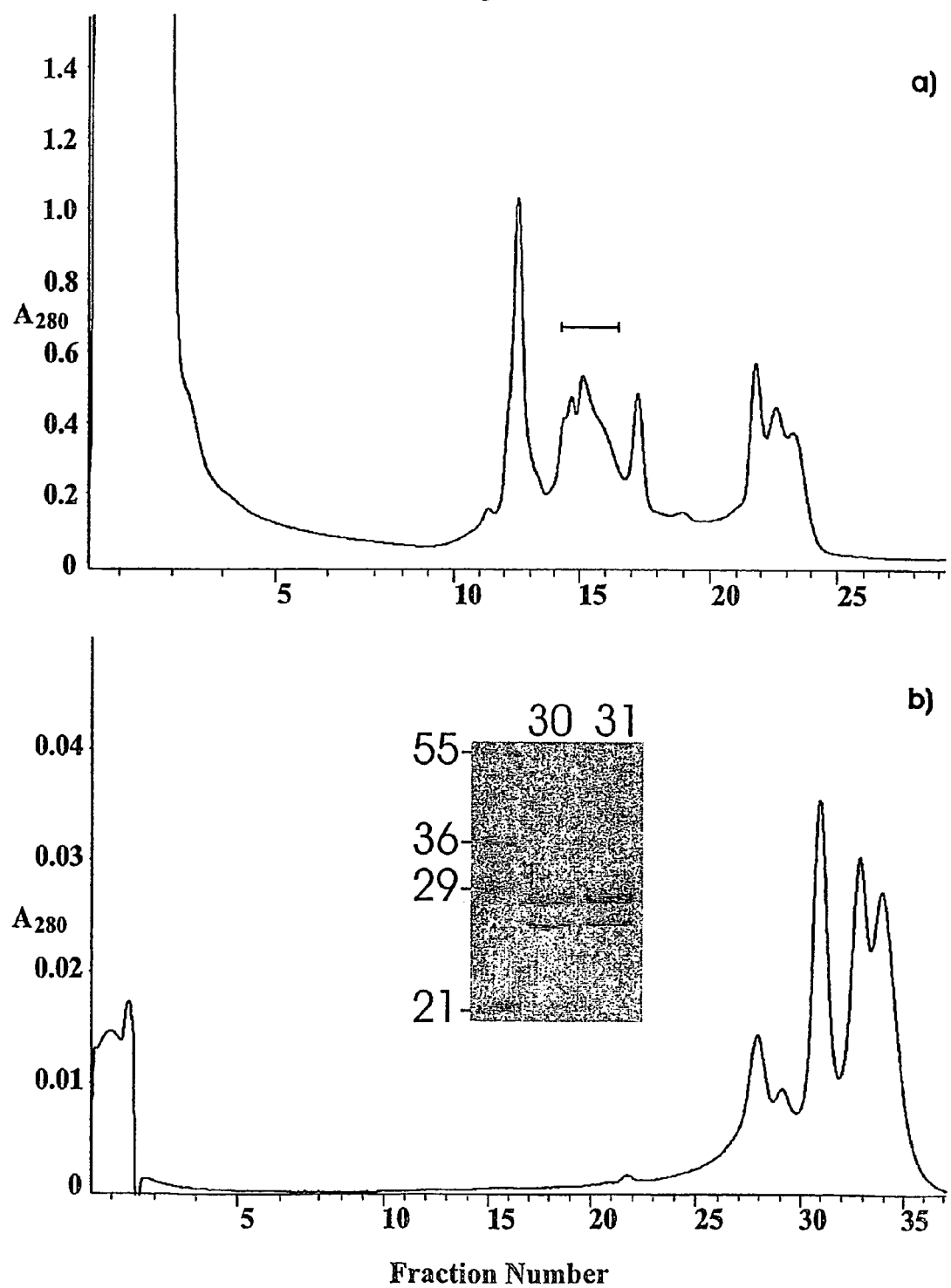
FIG. 1. Purification and analysis of PEB3. a) Cation-exchange chromatography of a glycine extract on MonoS column. PEB3 containing fractions were identified by N-terminal sequencing of SDS-PAGE bands, pooled as indicated, dialyzed and freeze-dried. b) Re-fractionation of pooled material on MonoS column using a shallower gradient of 0-0.2 M NaCl. The inset shows SDS-PAGE analysis of fractions 30 and 31, which were identified as PEB3 containing fractions by N-terminal sequencing of SDS-PAGE bands.

The examples describe the isolation and the identification of the glycan moiety according to the present invention.

General Experimental Procedures

Bacterial strains and plasmids: *C. jejuni* NCTC 11168 was routinely grown on Mueller Hinton agar under microaerophilic conditions (10% $CO_2$, 5% $O_2$, 85% $N_2$) at 37° C. *E. coli* DH10B (Invitrogen) was used as the host strain for cloning experiments and clones were grown on Luria S-gal agar (Sigma) or MH agar at 37° C. When appropriate, antibiotics were added to the following final concentrations: kanamycin 30 μg/mL and ampicillin 150 μg/mL. Plasmid pPCR-Script Amp (Stratagene) was used as the cloning vector.

Preparation of glycoprotein extracts: Cells from two plates of overnight growth were re-suspended in 10 mL Mueller Hinton broth and used to inoculate 1 litre of MH culture medium. Cultures were grown under microaerophilic conditions at 37° C. for 24 h with shaking at 150 rpm. Bacterial cells from 12 litres of culture media were harvested by centrifugation at 10,000×g for 15 min and immediately frozen at −75° C. Frozen cell pellets were thawed on ice in 0.2 M glycine HCl buffer, pH 2.2 (13), and extracted for 15 min with gentle stirring. Extracts were clarified by centrifugation at 10,000×g for 15 min, dialyzed against pure water (Milli-Q system, Millipore Corporation) and freeze-dried.

Purification and analysis of PEB3: The PEB3 protein was purified to homogeneity by cation exchange chromatography of the glycine extract as previously described (7). A Pharmacia MonoS HR 5/5 column was used on an ÅKTA Explorer LC system (Amersham Biosciences). The column eluate was monitored for UV absorbance at 280 nm and fractions were examined by SDS-PAGE analysis (21) in Mini Protean II slab gels (BioRad Laboratories). N-terminal sequencing of individual proteins was performed on a model 491 Procise protein sequencing system (Applied Biosystems Inc.), following transfer from SDS gels to ProBlot™ PVDF membrane (Applied Biosystems Inc.) as described by LeGendre et al. (22).

The protein molecular weight profiles of selected fractions were determined by electrospray ionization mass spectrometry using an Applied Biosystems/Sciex Q-Star hybrid quadrupole time-of-flight mass spectrometer. The fractions were first dialyzed extensively to remove salts, and adjusted to 30% methanol, 0.2% formic acid. The solution was infused at a flow rate of 1 μL/min and spectra were acquired over the range m/z 600>2000.

Analysis of tryptic peptides: Selected fractions were digested overnight at 37° C. with modified trypsin (Promega) in 50 mM ammonium bicarbonate and analyzed by capillary LC-tandem mass spectrometry using a capillary HPLC system (CapLC, Waters) coupled with a Q-TOF2 hybrid quadrupole time-of-flight mass spectrometer (Micromass). Approximately 250 ng of each digest was injected on a 0.3×150 mm PepMap $C_{18}$ capillary LC column (Dionex/LC-Packings) and resolved by gradient elution (5-90% acetonitrile, 0.2% formic acid in 45 minutes). The mass spectrometer was set to operate in automatic MS/MS acquisition mode and spectra were acquired on doubly, triply and quadruply charged ions.

Larger scale separation of the tryptic digest was carried out on a 4.6 mm×250 mm Jupiter $C_{18}$ LC column (Phenomenex Inc.). The fraction containing the glycopeptide was then infused at a flow rate of 1 μL/min into the microelectrospray interface of the Q-TOF2 mass spectrometer. Fragmentation of the glycopeptide prior to MS/MS analysis was achieved by front-end collision-induced dissociation (the orifice voltage was increased to 100 V from the normal 40 V). The MS/MS collision offset for the singly charged fragment ions produced in this manner was 20-25 V (lab frame of reference). For β-elimination experiments by the method of Rademaker et al. (23), approximately half of the glycopeptide-containing fraction was evaporated to dryness and dissolved in 25% aqueous ammonium hydroxide. The solution was left at room temperature overnight, evaporated to dryness for a second time and re-dissolved in water. The solution was then examined by infusion-MS as described above.

Purification and analysis of total glycoproteins: The glycoproteins from the glycine extracts were isolated by affinity chromatography on SBA lectin/agarose (Sigma-Aldrich Ltd.). The freeze-dried glycine extract was redissolved in PBS (100 mM NaCl, 50 mM sodium phosphate pH 7.5) and passed through an SBA/agarose column previously equilibrated in PBS. The column was washed with 10 column volumes of PBS and bound glycoprotein was eluted with 0.1 M GalNAc in PBS. Glycoprotein-containing fractions were pooled, dialyzed against Milli-Q water and freeze-dried.

The glycoproteins were separated by SDS-PAGE on 12.5% homogeneous polyacrylamide gels (21). 2D-PAGE was performed using pre-cast IEF strips containing immobilized linear pH gradients of either pH 3-10, pH 4-7 (BioRad Laboratories) or pH 6-11 (Amersham Biosciences). Proteins were solubilized in sample buffer according to the manufacturer's instructions and resolved by isoelectric focussing on the pre-cast IEF strips followed by SDS-PAGE on homogenous 12.5% slab gels, 20×20 cm, for the second dimension. Gels were stained with Bio-Safe colloidal G-250 Coomassie blue stain (BioRad Laboratories) or silver stained (23). For subsequent lectin probing, the gels were electroblotted onto PVDF membrane at 50 V for 1 h in 10 mM 3-(cyclohexylamino)-1-propane sulphonic acid buffer, pH 11, containing 10% methanol. The membrane was washed in Milli-Q water and blocked in Tris-buffered saline (100 mM NaCl, 50 mM Tris pH 7.5) with 0.05% Tween 20 and 2% blocking buffer (Roche Molecular Biochemicals) for 2 h at room temperature. Following blockage, blots were further incubated with SBA-alkaline phosphatase conjugate (EY Laboratories Inc.) at a concentration of 10 μg/mL in the above blocking solution for 1 h at room temperature. Blots were washed three times in Tris-saline with 0.05% Tween 20 and developed using nitro blue tetrazolium chloride (NBT) and 5-bromo-4-chloro-3-indolyl phosphate (BCIP) in 0.1 M NaCl, 0.1 M Tris pH 9.5 with 50 mM $MgCl_2$.

MS analyses of 2D-gel spots: The protein spots were excised and destained with a 1:1 ratio of 30 mM potassium ferricyanide and 100 mM sodium thiosulfate (24). The gel spots were washed extensively with deionized water, shrunk with acetonitrile, re-swollen with 50 mM ammonium bicarbonate containing Promega modified trypsin (10 ng/μL) and sufficient 50 mM ammonium bicarbonate was added to cover the gel pieces (typically 30 μL). The tubes were sealed and incubated overnight at 37° C. The digest solutions were removed and the gel pieces were extracted with 50 μL of 5% acetic acid and then with 50 μL of 5% acetic acid in 50% aqueous methanol. The extracts were pooled with the digest solutions and concentrated to approximately 10 μL.

The peptide extracts from the intense protein spots were analyzed by MALDI-TOFMS using a MALDI-LR mass spectrometer (Micromass). Approximately 0.5 μL of the MALDI matrix solution (10 mg/mL α-cyano-4-hydroxy-cinnamic acid in 50% acetonitrile, 0.2% TFA) was deposited on the target plate and allowed to dry. The peptide extracts were desalted using $C_{18}$ ZipTips™ (Millipore) and were deposited directly on the matrix spots. Acquisition of the MALDI-TOFMS spectra was carried out automatically. The spectra were calibrated externally using peptide standards and internally with trypsin autolysis peptides. Database searching was carried out in batch mode using Mascot Daemon™ (Matrix Science) and against the *C. jejune* NCTC11168 genome sequence database.

The extracts from the fainter protein spots were analyzed by nanoLC-MS/MS using the Q-TOF2 mass spectrometer. The entire samples were injected onto a 0.3×5 mm $C_{18}$ micro pre-column cartridge (Dionex/ LC-Packings). The peptides were retained while the sample solution was washed to waste. The trap was then brought online with a 75 μm×150 mm $C_{18}$ Nano-Series column (Dionex/LC-Packings) and the peptides were separated with a gradient supplied by the CapLC pump (15-75% acetonitrile, 0.2% formic acid in 30 minutes, approximately 300 nL/min flow rate). The mass spectrometer was set to acquire MS/MS spectra in automated mode as described above. Database searching was carried out as described for the MALDI-TOFMS analyses.

Glycopeptide preparation: Freeze-dried total glycoprotein (5 mg) was dissolved in 250 μL of 100 mM Tris pH 8.0 containing 2 mM $CaCl_2$, and digested with pronase as previously described (31). The digest was microfuged at 10,000×g for 15 min and the supernatant was applied to a column (1×120 cm) of BioGel P4, 200 mesh (BioRad Laboratories). The column was run in water and the column eluate was monitored by refractive index. Fractions were screened by ESIMS and precursor ion scanning mass spectrometry (precursors of the HexNAc oxonium ion at m/z 204) on an API 3000 triple quadrupole mass spectrometer (Applied Biosystems/Sciex). Fractions giving the HexNAc ion signature were pooled and freeze-dried. The glycopeptides were further purified on a 1×120 cm column of BioGel P2 fine grade, the fractions being monitored and screened as described above.

NMR spectroscopy: All spectra were acquired using a Varian Inova 600 MHz spectrometer using the standard Varian software. A gradient 4 mm indirect detection high-resolution magic angle spinning nano-NMR probe (Varian) with a broadband decoupling coil was used. The sample was spun at 3 KHz with dry nitrogen as the drive and bearing gas. The spin rate was not computer controlled but remained constant to within 10 Hz of the set value. Samples in 40 μL $D_2O$ solution were recorded at 25° C. and at 35° C. to produce sharper peaks. The pH was unknown due to the small volume. Deuterated EDTA (CDN Isotopes Inc.) was added to chelate metal ions and provide sharper peaks for bacillosamine and amino acids. Although the glycopeptide isolate from a P4 column contained some amino acid and sugar impurities, spectra were of sufficient quality to allow complete resonance assignments of the glycopeptide in the presence of 15 mM of deuterated EDTA. Much of the NMR structural work proceeded with this sample because of the risk of loosing the bulk of the isolated glycopeptide by further purification. The derived structure was confirmed by additional NMR experiments on glycopeptide that had been purified using a P2 column, lyophilized, and dissolved in 40 μL $D_2O$ with 1 mM deuterated EDTA. The experiments were performed with suppression of the HDO signal at 4.78 ppm (25° C.) and 4.67 ppm (35° C.). Acquisition and processing of two-dimensional experiments (COSY, TOCSY, NOESY, HMQC, HMBC) were performed as described previously (32). The $^1H$ reference was set by external acetone at 2.23 ppm. The $^{13}C$ reference was set with the methyl resonance of external acetone at 31.07 ppm. The $^1H$ and $^{13}C$ chemical shifts in Table 1 were measured from the proton spectra and from C-H cross peaks in the HMQC and HMBC spectra. 1D TOCSY experiments with various spin-lock times from 30-151 ms and 1D NOESY with mixing times from 400-800 ms were performed as described previously (25,26). Selective experiments were described as 1D EXP(selected spins, selective excitation bandwidth, mixing time) where EXP is TOCSY or NOESY.

The use of magic angle spinning (MAS) for liquid state samples in the presence of both RF and magnetic-field homogeneities has been shown to influence significantly the performance of mixing sequences in TOCSY experiments and can degrade performance (27,28). Using adiabatic (WURST) mixing sequences can eliminate such effects (27,29). The standard 2D TOCSY and 1D TOCSY sequences were modified so that the MLEV-17 or DIPSI-2 mixing sequence was replaced with the adiabatic WURST-2 pulses. The adiabatic (WURST-2) mixing had a single adiabatic inversion pulse length of $T_p$=1/MAS spin rate, a modulation depth of 8 and an adiabicity of 2. Typically, for the WURST-2 pulse, the sweep bandwidth was 24 kHz, $T_p$=0.333 ms (at a MAS spin rate of 3000+/−10 Hz), $B_1$(max)=8.51 kHz, $B_1$ (RMS)=4.77 kHz.

GC-MS analysis: The enantiomeric configurations of the Glc and GalNAc components of the P2 product were assigned by characterization of the but-2-yl glycosides in gas liquid chromatography-mass spectrometry (21). The derivatives were analyzed using a Hewlett-Packard chromatograph equipped with a 30 m DB-17 capillary column (180° C. to 260° C. at 3.5° C./min), and spectra in the electron impact mode were obtained with a Varian Saturn II mass spectrometer.

Construction and characterization of pglB mutant: For construction of the pglB mutant, genes Cj1121c to Cj1126c were PCR amplified from *C. jejuni* NCTC 11168 using the primers: Cj1121cF (5'-ACTCACTATTGCCATTAA-GATAAGC-3'; SEQ ID NO:3) and Cj1126cR (5'-AAAAC-CCTTATTTAGTTTTGTTTGC-3'; SEQ ID NO:4). The PCR product was polished with Pfu polymerase and then ligated into pPCR-Script Amp (Stratagene) according to the manufacturer's instructions. The ligation mixture was electroporated into electrocompetent *E. coli* DH10B and selected for on LB S-gal agar (Sigma-Aldrich) with ampicillin. A blunt-ended kanamycin resistance cassette from pILL600 (37) was inserted into the filled-in XbaI restriction site of pglB, generating pEAp26. The orientation of the cassette was determined by sequencing with the ckanB primer (5'-CCTGGGTTTCAAGCATTAG-3'; SEQ ID NO:10). DNA was sequenced using terminator chemistiy and AmpliTaq cycle sequencing kits (Applied Biosystems) and analysed on an Applied Biosystems 373 DNA sequencer. The mutated plasmid DNA was used for electroporation into *C. jejuni* NCTC 11168 (32) and the kanamycin-resistant transformants were characterized by PCR to confirm that the incoming plasmid DNA had integrated by a double cross-over event.

Proteins were extracted from *C. jejuni* whole cells using 0.2 M glycine at pH 2.2 (10) and dialysed against water. Samples were analyzed by 2D-PAGE using 11 cm pH 3-10 ReadyStrip IPG strips (BioRad Laboratories) and pre-cast 12×8 cm 8-16% gradient Criterion slab gels (BioRad Laboratories). Gels were stained with colloidal coomassie blue, photographed, and then partially destained by washing in water. Proteins were transferred for 1 h at 207 mA onto PVDF membranes using a Trans-Blot SD Semi-Dry Transfer Cell (BioRad). After blocking overnight, membranes were probed with a 1:500 dilution of HS:2 serotyping serum followed by a 1:5000 dilution of goat anti-rabbit antiserum (Sigma-Aldrich), and developed with NBT/BCIP (Roche Molecular Biochemicals).

Experimental Procedures for the Detection of Glycans from *Campylobacter* Cells

Bacterial strains and growth conditions: *Campylobacter jejuni* NCTC11168 (HS:2) was isolated from a case of human enteritis (46) and later sequenced by Parkhill et al. (6). *C. jejuni* serostrains: HS:1 (ATCC 43429), HS:2 (ATCC 43430), HS:3 (ATCC 43431), HS:4 (ATCC 43432), HS:10 (ATCC 43438), HS:19 (ATCC 43446), HS:36 (ATCC 43456) and HS:41 (ATCC 43460) were obtained from ATCC; *C. jejuni* HS:23 was obtained from Dr. Peggy Godschalk, Erasmus University Medical Center, Rotterdam; *C. jejuni* OH4382 and OH4384 were obtained from Health Canada; and *C. coli* HS:30 (NCTC 12532) was obtained from NCTC. All *campylobacter* strains were routinely grown on Mueller Hinton agar (Difco) under microaerophilic conditions at 37° C. *C. jejuni* NCTC11168 mutants were grown on Mueller Hinton agar with 30 μg/mL kanamycin.

Construction and characterization of site-specific mutations: Construction of the *C. jejuni* NCTC11168 kpsM (12) and pglB (13) mutants has already been described.

Preparation of cells for HR-MAS NMR: *C. jejuni* overnight growth from one agar plate (~$10^{10}$ cells) was harvested and suspended in 1 mL of 10 mM potassium buffered saline (pH 7) made in $D_2O$ containing 10% sodium azide (w/v). The suspension was incubated for 1 h at room temperature to kill the bacteria. The cells were pelleted by centrifugation (7 500×g for 2 min) and washed once with 10 mM potassium buffered saline in $D_2O$. The pellet was resuspended by adding 20 μL of $D_2O$ and then 40 μL of the suspension was inserted into the rotor for analysis.

HR-MAS NMR spectroscopy: HR-MAS experiments were performed using a Varian Inova 600 MHz spectrometer equipped with a Varian nano-NMR probe as previously described (12,13). Spectra from 40 μL samples were spun at 3 KHz and recorded at ambient temperature (21° C.). The experiments were performed with suppression of the HOD signal at 4.8 ppm. Proton spectra of bacterial cells were acquired with the Carr-Purcell-Meiboom-Gill (CPMG) pulse sequence [90-(τ-180-τ)$_n$-acquisition] (34) to remove broad lines arising from lipids and solid-like material. The total duration of the CPMG pulse (n*2τ) was 10 ms with τ set to (1/MAS spin rate). One-dimensional selective TOCSY experiments with various spin-lock times from 30-150 ms and selective NOESY with mixing times from 100-400 ms were performed as described previously (25,35). For use under MAS conditions, the TOCSY sequences were modified so that the DIPSI-2 mixing sequence was replaced with the adiabatic WURST-2 pulses (13). Selective experiments were described as EXP[selected spins, selective excitation bandwidth, mixing time] where EXP is TOCSY or NOESY. Typically, proton spectra of bacterial cells could be obtained using 256 to 1024 transients (15 min to 1 hour). For the selective experiments on the N-linked glycan resonances present as a minor component in the bacterial cells, the time for each TOCSY and NOESY varied from 1 to 8 hours.

EXAMPLES

Example 1

Purification and Characterization of PEB3

PEB3 protein (Cj0289c) was identified in 2D gels of a glycine extract by peptide mass fingerprinting, as a component of a group of spots focussing within a range of pH 9-10 (results not shown). PEB3 was purified from the extract by cation exchange chromatography, and re-fractionated on the same column, using a shallower NaCl gradient, resulted in the PEB3 appearing in three fractions (FIG. 1). SDS-PAGE analysis showed two bands, whose N-terminal sequences were determined following their transfer to a PVDF membrane. Ten cycles of sequencing identified the lower mass species as PEB3 while the higher mass, more abundant component, was also PEB3 with a minor sequence corresponding to PEB4 (Cj0596).

Figure 2:
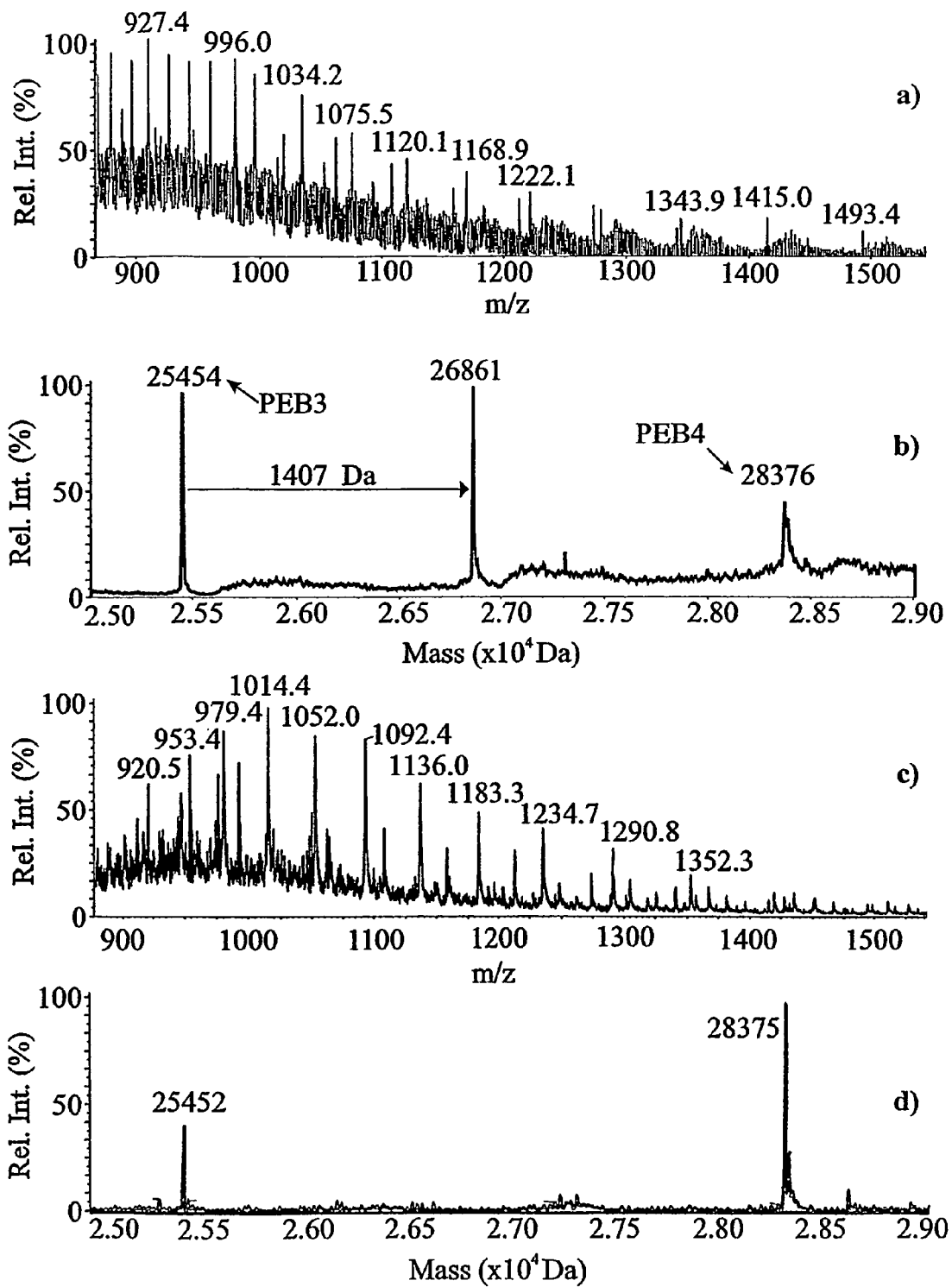
FIG. 2. ESI-MS analysis of fractions from cation exchange chromatography purification of PEB3. a) ESI-MS of the fraction 31 of FIG. 1, after dialysis and the reconstructed molecular mass profile obtained from this spectrum. b) The peaks at 25,454 and 28,376 Da were identified as PEB3 and PEB4, respectively. Further analysis was required to identify the third peak at 26,861 Da as glycosylated PEB3. c) ESI-MS of PEB3 similarly purified from the pglB mutant, and the reconstructed mass profile, d) showing the lack of the glycosylated form of PEB3.

The mass spectrum and the reconstructed molecular mass profile for fraction # 31 are presented in FIG. 2a) and b). Three peaks were observed in the reconstructed mass profile. The peaks at 25,454 Da and 28,376 Da correspond well with the expected molecular masses of PEB3 (25,453 Da, Cj0289c) and PEB4 (28,377 Da, Cj0596) respectively, without signal peptides. To identify the protein of mass 26,861 Da, CapLC-MS/MS analysis was carried out on the tryptic digest of this fraction. All but one of the peptides identified could be assigned to PEB3 or PEB4, in accord with the N-terminal sequence data. MS/MS analysis of the unidentified ion (FIG. 3a) clearly identifies it as a glycopeptide. A fragmentation series composed of sequential losses of HexNAc (203 Da) and a single Hex (162 Da) can be observed in this spectrum. The tryptic peptide was identified as $^{68}$DFNVSK$^{73}$ (SEQ ID NO:2) from PEB3. The residue mass of the oligosaccharide portion of this glycopeptide is 1406 Da, which corresponds well with the difference in the molecular weights of PEB3 and the unknown protein peak observed in FIG. 2b. Therefore, it appeared that approximately 50% of the PEB3 protein in this fraction was modified with a single oligosaccharide composed of 5 HexNAcs, 1 Hex and an unusual sugar with a residue mass of 228 Da. Moreover, the MS/MS spectrum indicated that the oligosaccharide was linked to the peptide via the 228 Da sugar moiety.

Example 2

Characterization of the Glycopeptide Linkage

Figure 3:
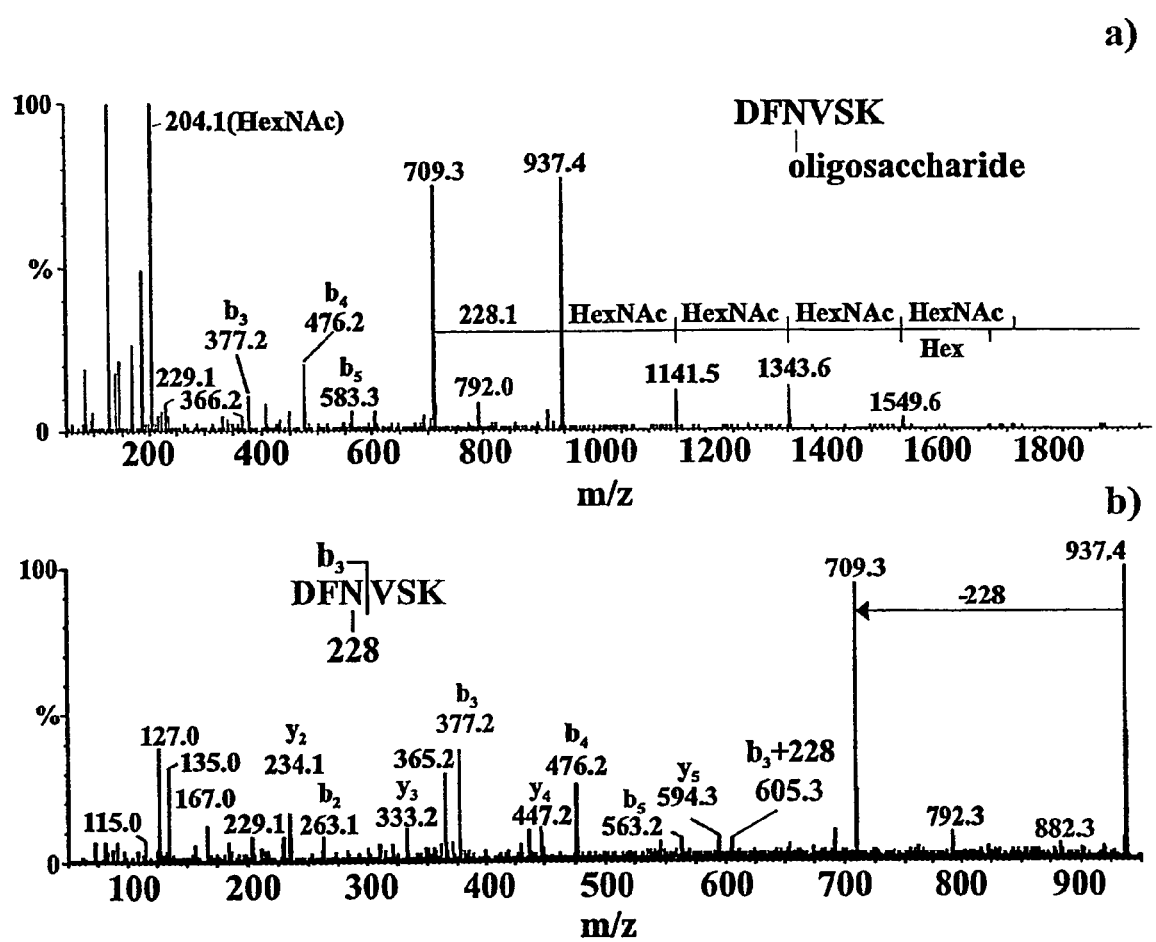
FIG. 3. MS/MS analysis of the PEB3 tryptic glycopeptide. a) Product ion spectrum of the doubly protonated glycopeptide ion at m/z 1057.9. The fragment ions originating from the sequential loss of oligosaccharide residues are indicated in the spectrum. The peptide sequence (SEQ ID NO:1) is shown in the inset. b) Second generation product ion spectrum of the glycopeptide fragment (SEQ ID NO:2) ion at m/z 937.4. The glycopeptide was fragmented by front end collision induced dissociation (orifice voltage =100 V) as it entered the mass spectrometer. The observation of the $b_3+228$ fragment ion at m/z 605.3 confirmed that the oligosaccharide is N-linked.

The PEB3 tryptic peptide to which the oligosaccharide is attached contains sites for both N- and O-linkage, ie Asn and Ser. Therefore, it was necessary to carry out further experiments to determine the nature of this linkage. Previously, we have used β-elimination to remove O-linked carbohydrates from the flagellin of C. jejuni 81-176 (5). However, this procedure failed to remove the oligosaccharide in this instance. This was our first indication that the oligosaccharide is N-linked. This was confirmed by MS/MS analysis of the singly protonated fragment ion at m/z 937.0 produced by front-end collision-induced dissociation of the intact glycopeptide (FIG. 3b). This ion is composed of the tryptic peptide plus the unusual 228 Da sugar only. An ion was observed at m/z 605.1 which could only be assigned to the $b_3$ fragment ion plus the 228 Da sugar moiety. No fragment ions were observed to suggest that the carbohydrate is linked to the serine residue. All of this evidence strongly suggests, that the oligosaccharide is linked to the peptide at Asn70. Interestingly, this peptide contains the eukaryotic N-linkage consensus sequon, Asn-Xaa-Ser.

Example 3

Isolation and Identification of Glycoproteins

Putative glycoproteins were purified by SBA affinity chromatography from the glycine extracts of 40 g wet weight of cells. The yield of putative glycoproteins was 5 mg as estimated by UV absorbance at 280 nm. The GalNAc eluant was subjected to 1D- and 2D- PAGE (FIG. 4) and to ensure that the proteins purified in this manner possessed lectin binding properties, rather than non-specific binding characteristics, western blotting with an SBA/alkaline phosphatase conjugate was also carried out. Approximately 13 protein species were visualized following 1D SDS-PAGE but this number increased substantially when the product was analyzed by 2D-PAGE. The proteins in individual bands from 1D SDS-PAGE and spots from 2D-PAGE were identified by mass fingerprinting and database searching (Table I). Among the identified proteins are PEB3 (Cj0829c) and CgpA (Cj1670c) previously identified by Linton et al. (8). The vertical pattern of spots with identical pis displayed by Cj1670c, and other proteins, likely indicates varying degrees of glycosylation since examination of their predicted amino acid sequences, derived from the whole genome sequence of C. jejuni NCTC 11168 (6), revealed the presence of multiple potential N-linked glycosylation sites containing the sequon Asn-Xaa-Ser/Thr (Table I). In fact, MS/MS analysis of the Cj1670c-containing in-gel digest extracts indicated that 3 of its 6 N-linkage sites are occupied to varying extents (three Cj1670c glycopeptides were detected by capLC-MS/MS: $^{7}$TDQNITLVAPPEFQKEEVK$^{25}$ (SEQ ID NO:5), $^{77}$VLDVSVTIPEKNSSK$^{91}$ (SEQ ID NO:6) and $^{92}$QES NSTANVEIPLQVAK$^{108}$ (SEQ ID NO:7). A single glycopeptide was also observed for Cj0114 ($^{71}$LSQVEENNQNIEN NFTSEIQK$^{91}$; SEQ ID NO:8) and for Cj0200c ($^{1}$DSLKLEGTIAQIYDNNK$^{17}$; SEQ ID NO:9). Furthermore, the mass and composition of the glycan component of all these glycopeptides appears to be identical to that observed for PEB3.

However, certain proteins identified from the 2D-PAGE, notably Cj0147c, Cj0169, Cj0332c, Cj0334, Cj0638c, Cj1181c and Cj1534c do not contain any of these specific sequons in their amino acid sequences. These proteins either are non-covalently associated with SBA-binding proteins or bind non-specifically to the column. This conclusion is supported by the failure of these protein spots to react with the SBA/alkaline phosphatase conjugate following 2D PAGE and electroblotting (Table I).

Example 4

Preparation of Glycopeptides

Figure 5:
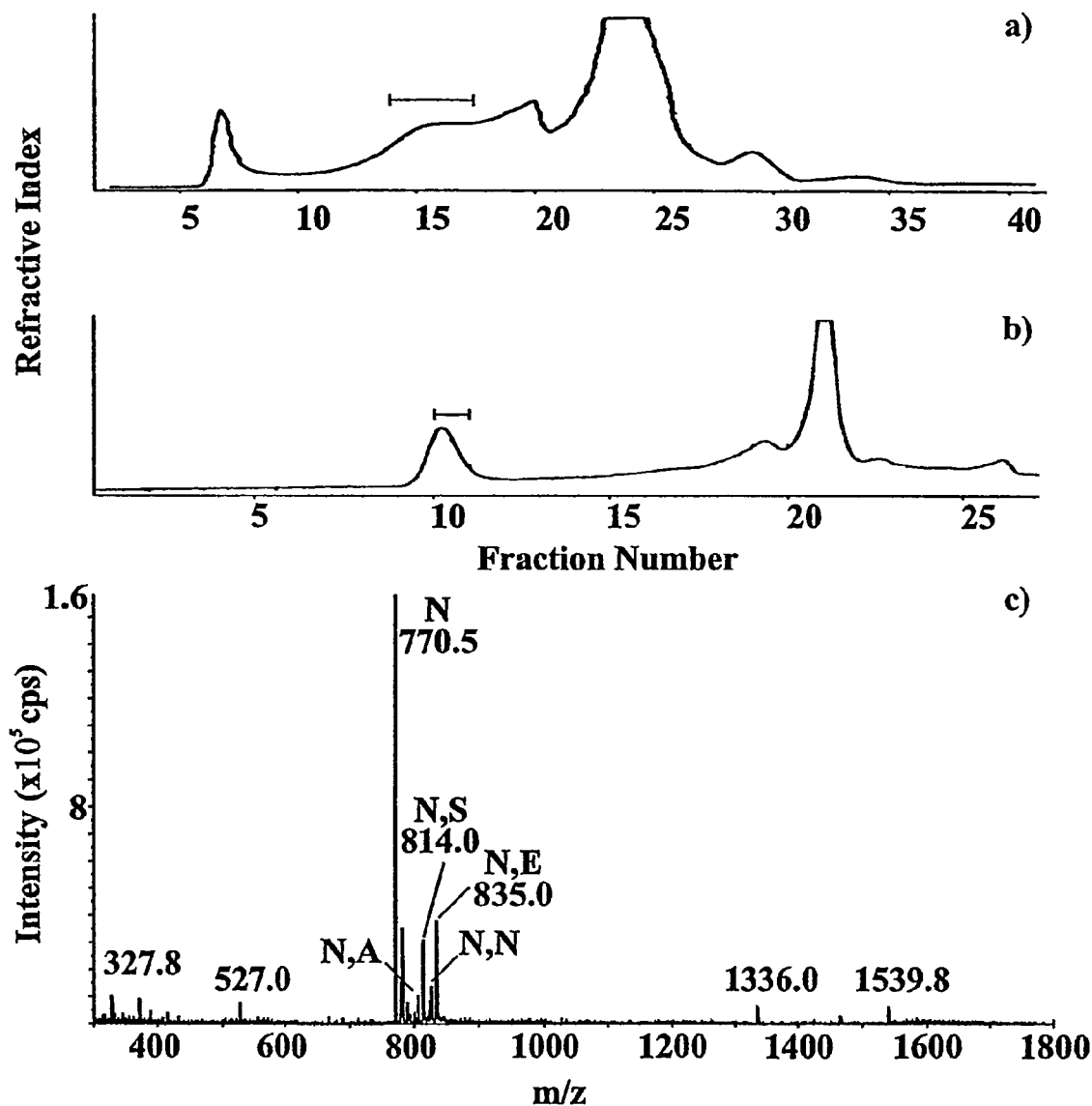
FIG. 5. Purification of glycopeptides from a pronase digest of the SBA affinity chromatography product. a) Size exclusion chromatography on BioGel P4 200 mesh of the pronase digest. b) Re-fractionation of pooled material from P4 on BioGel P2 fine grade. In both fractionations, glycoprotein-containing fractions were identified by MS and pooled as indicated by the bars. c) ESI-MS spectrum of fraction 10 from B above. The doubly protonated ion ($MH_2^{2+}$) at m/z 770.5 corresponds to the heptasaccharide linked to Asn. A number of larger ions are also observed and are due to the addition of a second amino acid residue. The amino acid compositions of the major glycan-containing ions are indicated on the spectrum.

The mixed glycoprotein sample was subjected to two rounds of pronase digestion and the products were separated by gel filtration on BioGel P4 (FIG. 5a). The carbohydrate-containing fractions were located by mass spectrometry and, after NMR studies (see below), the sample was re-purified on BioGel P2 (FIG. 5b). The final purified sample was composed mainly of the oligosaccharide linked to a single Asn (FIG. 5c). There was no evidence of any variation in the glycan component. The yield of glycopeptides was estimated at around 200 µg.

Example 5

Preparation of Isolated Heptasaccharide

The heptasaccharide moiety identified in Example 4 (Formula I) may be obtained in isolation by known methods. For example, the amino acid moiety (Asn) may be cleaved from the oligopeptide prepared in Example 4 by enzymatic or chemical hydrolysis well known in the art. It may be noted that although the present inventors have not carried out the above step, it would be evident that such a step may be carried out to isolate the heptasaccharide. The heptasaccharide can also be obtained directly from the glycoprotein without going through any glycopeptide. This cleavage can also be performed by enzymatic or chemical hydrolysis. For example Patel et al. (41) teach the use of hydrazine for such cleavage.

Example 6

NMR Spectroscopy

Figure 6:
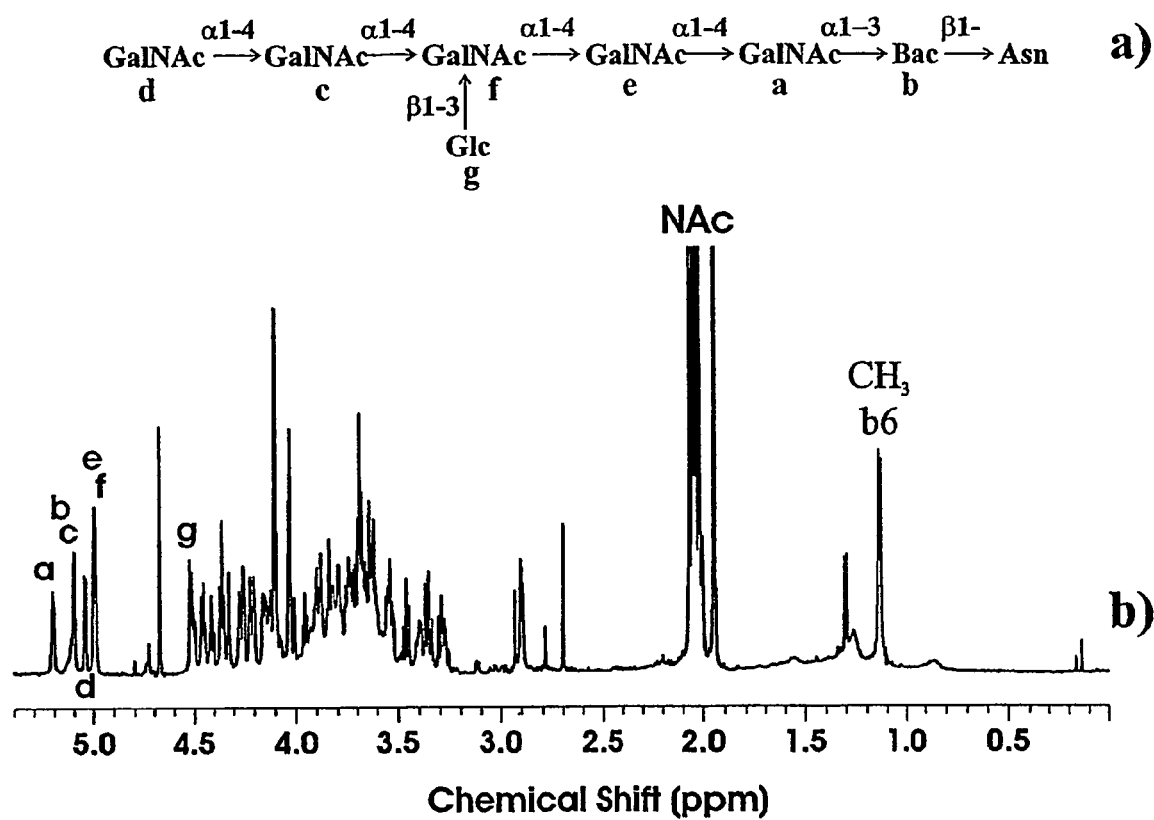
FIG. 6. Structure and $^1H$ spectra of the glycopeptide. a) Deduced structure of the glycopeptide. b) Spectrum after final purification on a P2 column ($D_2O$, 35° C., 1 mM deuterated EDTA). The anomeric sugar resonances in the region 4.4 to 5.4 ppm are labeled.
Figure 7:
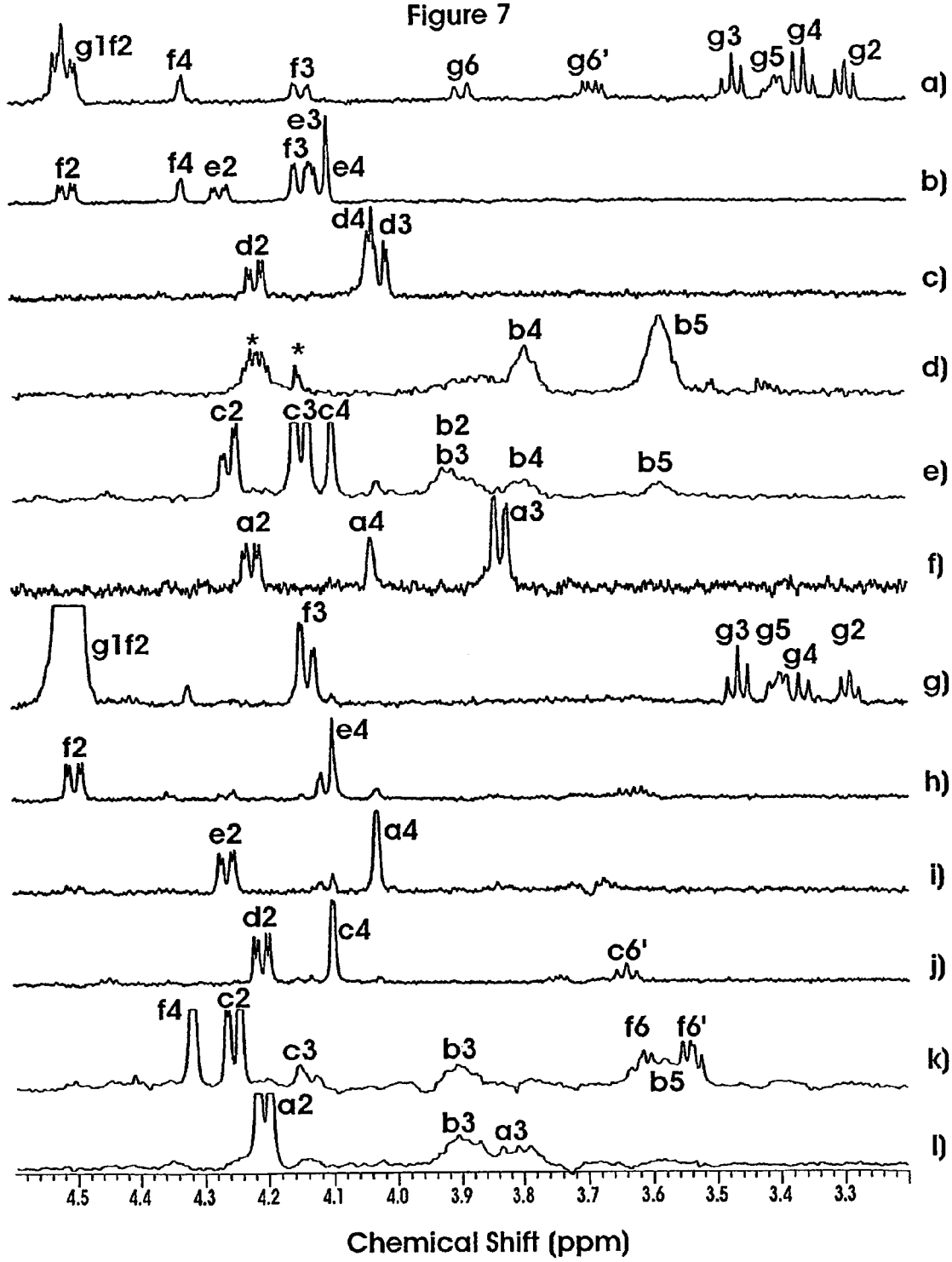
FIG. 7. 1 D selective NMR experiments with the glycopeptide. a) 1D TOCSY(g1f2, 15 Hz, 144 ms), b) 1D TOCSY (e1f1, 25 Hz, 144 ms), c) 1D TOCSY(d1, 20 Hz, 144 ms), d) 1D TOCSY(b6, 50 Hz, 66 ms) where * is a peptide resonance, e) 1D TOCSY(b1c1, 40 Hz, 151 ms), f) 1D TOCSY(a1, 25 Hz, 144 ms), g) 1D NOESY(g1f2, 15 Hz, 400 ms), h) 1D NOESY(f1, 10 Hz, 400 ms), i) 1D NOESY(e1, 10 Hz, 400 ms), j) 1D NOESY(d1, 20 Hz, 400 ms), k) 1D NOESY(b1c1, 40 Hz, 400 ms), l) 1 D NOESY(a1, 40 Hz, 400 ms).

With the use of selective methods, it was possible to work with the impure P4 sample. The complete resonance assignment of the sugar moiety was done with this sample for fear of loss of glycopeptide upon further purification. After a second purification using a P2 column, 25% of the glycopeptide was lost as judged by measurement of the S/N ratio for the P4 and P2 purified samples. An HMQC experiment was rerun on the P2 purified sample to confirm the assignments obtained using the P4 purified sample. From mass spectrometry results, the glycopeptide was composed of 5 HexNAc residues, a Hex residue, and an unknown sugar with a mass of 228 Da. The absolute configuration of the HexNAc and Hex residues was determined to be D by chemical analysis. Analysis of the $^1$H and $^{13}$C NMR data indicated the presence of 8 anomeric protons labeled in alphabetical order (FIG. 6). A series of 1 D TOCSY for the anomeric resonances was done for proton assignments (FIG. 7). Different mixing times were used to assign the spins within each residue. HMQC and HMBC were then used to assign the $^{13}$C resonances. The NMR assignments are given in Table II. 1D NOESY experiments (FIG. 7) were used to obtain the sequence as shown (FIG. 6).

Residue g was assigned to β-D-Glcp. For the 1D TOCSY of g1 with a mixing time of 144 ms (FIG. 7a), all spins up to the H6 and H6' resonances were detected, indicative of the large $J_{H,H}$ couplings typical of β-glucopyranose. Resonance g1 also overlapped with f2, allowing detection of the f1 to f4 resonances. Residue g was terminal due to similar $^{13}$C and $^1$H chemical shifts for C2 to C6 with those of β-D-glucopyranose (36).

Five residues (a, c, d, e, and f) were identified as α-D-GalpNAc. A value of $J_{1,2}$ of 3.6+/−0.2 Hz, the strong H1-H2NOE (FIG. 7), and $J_{H,H}$ coupling pattern which included a small coupling to H4 (FIG. 7) showed that these units had the α-D-galactopyranosyl configuration. Although, the e1 and f1 anomerics resonances could be selectively excited with a narrow bandwidth of 10 Hz, the spectra for simultaneous excitation of e1 and f1 are shown in FIG. 7b. Resonances f2 to f4 were also detected for the 1D TOCSY of g1f2 (FIG. 7a). A chemical shift for C2 near 51 ppm was indicative of an acetamido group. The (C2, H4) HMBC correlations were used to assign the C2 resonances of the five GalNAc residues. The 1D TOCSY-NOESY(H1, H4) was used to detect the NOE between H4 and H5 and thus assign the H5 resonances (25). The 1 D-TOCSY experiments on the H5 resonances were then used to detect the H6s resonances (not shown). Integration of the P2 purified sample (FIG. 6b) indicated 7 NAc groups, five of those corresponding to the five GalNAc residues. Comparison of the $^{13}$C chemical shifts of the GalNAc units with those of α-D-GalpNAc indicated that residues a, c, e, f were linked at O-4 due to downfield shifts for C4 (37). Residue f had a branch point at O-3 as established by a downfield shift for C3. Residue d was terminal due to similar $^{13}$C chemical shifts for C2 to C6 with those of α-D-GalpNAc (37).

Residue b was assigned to β-D-bacillosamine (2,4-diacetamido-2,4,6-trideoxy-β-D-glucopyranose). For residue b and c, the anomeric resonances partially overlapped. For the 1D TOCSY of the b1 and c1 resonances with a mixing time of 144 ms (FIG. 7e), broad resonances could be identified up to a $CH_3$ resonance (b6) at 1.14 ppm. For the 1D TOCSY for b6 at 1.14 ppm, with a mixing time of 66 ms (FIG. 7d), peaks up to b4 were observed. A series of 1D TOCSY with different mixing time from 30 ms to 144 ms were done to assign the peaks. For residue b, the broad peaks do not provide the coupling constants. However, for the 1D TOCSY of b1 with a mixing time of 144 ms, resonances up to H6 could be observed, similar to the 1D TOCSY for H1 of β-Glcp (residue g). Hence, such efficient transfer was indicative of large coupling constants typical of a β-glucopyranosyl configuration. The b1-b3 and b1-b5 NOEs observed in FIG. 7k were also typical of the β anomeric configuration. Chemical shifts for C2 and C4 at 55 and 58 ppm were indicative of acetamido groups, in accord with the presence 7 NAc groups in the structure (FIG. 6a). The chemical shift for C1 at 79 ppm and H1 at 5.1 ppm indicated an N-linked anomeric similar to that found for β-GlcNAc-Asn (20). Comparison of the chemical shifts of residue b with those of 2,4-diamino-2,4,6-trideoxy-β-D-glucopyranose found in other structures indicated that Bac was linked at O-3, the only possible glycosidation site (38-40).

The absolute configuration of residue b was obtained by NOEs as previously described for another structure containing bacillosamine (38). A strong NOE observed between the $CH_3$ resonance at 1.14 ppm (b6) and the NAc at 1.95 ppm was due to the close proximity of the $CH_3$ group at C6 to the NAC-$CH_3$ group at C4. Since, the NAc resonance at 1.95 ppm was isolated from the other NAC resonances it could be selectively excited. A strong NOE was observed between this NAc resonance and the α-D-GalpNAc H1 resonance of residue a, due to the a(1-3)b linkage as shown below. This NOE can only occur if residue b has the D-configuration, where the NAc group at C4 of residue b is in close proximity (3 Å) to the anomeric proton of residue a. This NOE is not possible if residue b has the L-configuration, since the H1a/4b-NAc interproton distances are greater than 5 Å.

The sequence was determined by 1D NOESY experiments (FIG. 7). The strong c1-f4 NOE and smaller c1-f6 and c1-f6' NOEs established the c(1-4)f linkage. The strong d1-c4 NOE and a smaller d1-c6' indicated the d(1-4)c sequence. The e1-a4, f1-e4 and g1-f3 established the e(1-4)a, f(1-4)e and g(1-3)f linkages. The a1-b3 NOE (FIG. 7I), established the a-b sequence. The structure is shown in FIG. 6a. The sequence is in accord with the glycosidation shift observed for the linkage carbons (see above).

Example 7

Characterization of a pglB Mutant

Figure 4:
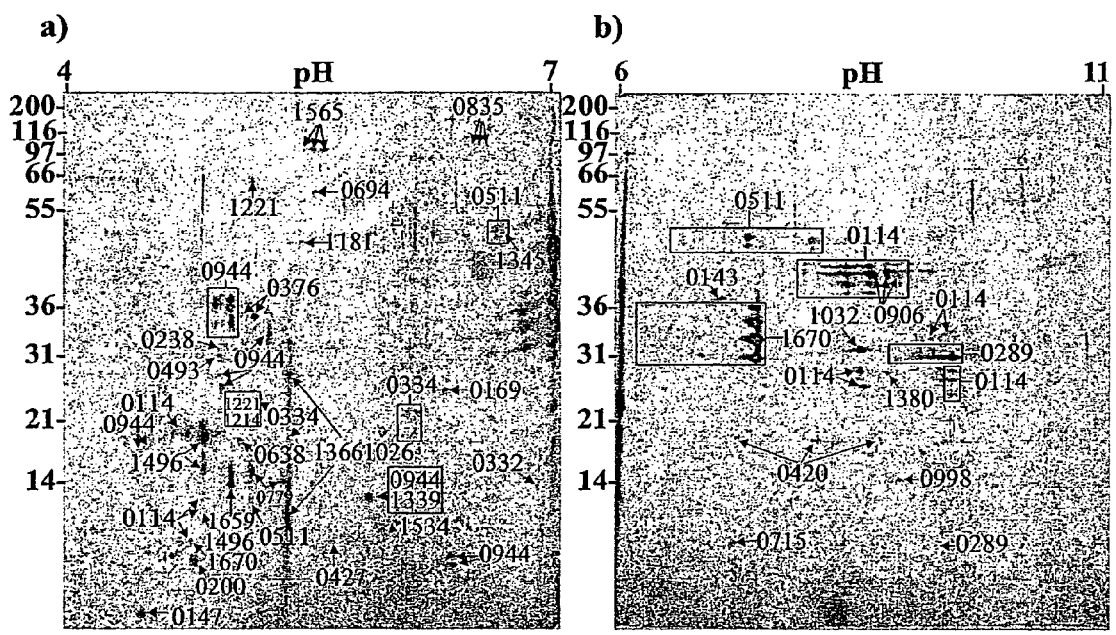
FIG. 4. 2D gels of the SBA affinity chromatography product. The proteins were separated on 2D-PAGE in two pH ranges, a) pH 4-7 and b) pH 6-11, and then silver-stained. The identities of the spots, shown by their Cj numbering, were determined by mass spectrometry of their tryptic digests. A full list of the identified proteins is given in Table I.
Figure 8:
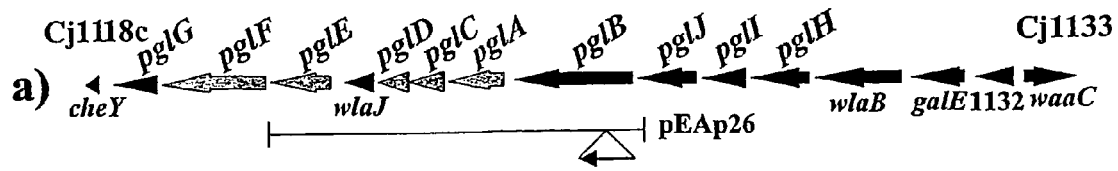
FIG. 8. The pgl locus and characterization of the pglB mutant. a) Gene schematic of the general protein glycosylation locus of *C. jejuni* NCTC 11168. Genes which have homologues to genes in the pgl locus of *Neisseria* spp. are shown by grey arrows. The mutation in pglB shown below the locus was constructed using pEAp26. b) to e) Two dimensional gel analysis of *C. jejuni* wildtype and isogenic pglB mutant. b) and d) Colloidal coomassie stain of 2D gels before immunoblotting of wildtype and mutant, respectively. c) and e) Immunodetection of proteins by HS:2 serotyping sera of wildtype and mutant, respectively. The arrows indicate the proteins which showed differences in either gel migration and/or immunoreactivity which were excised for identification by mass fingerprinting. The identities of the spots are shown by their Cj numbering. The masses of the molecular weight protein markers in kDa are shown at the left.
Figure 8:
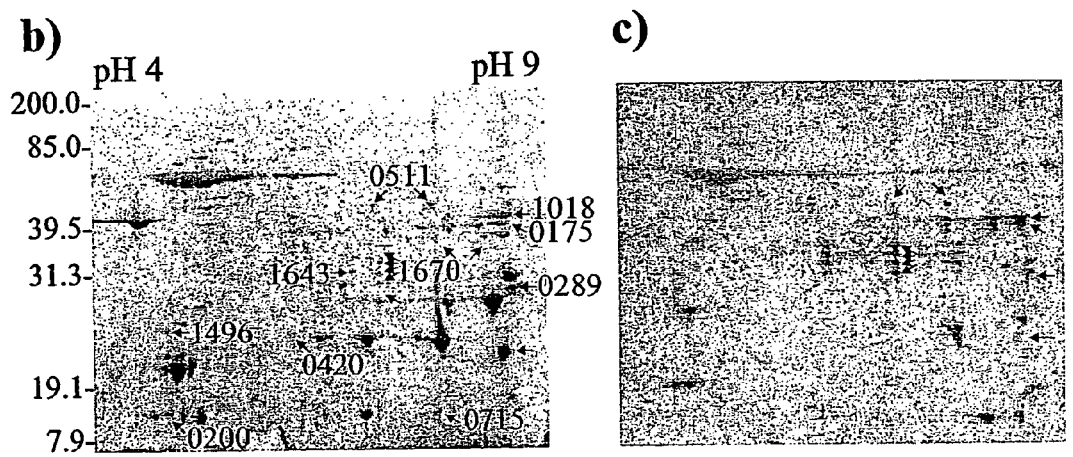
Figure 8:
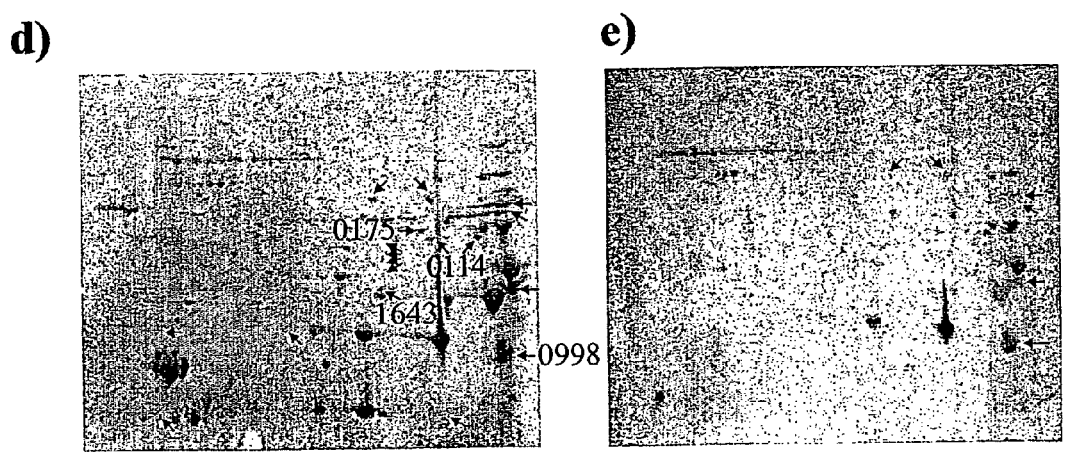

A pglB mutant was constructed by cassette mutagenesis (FIG. 8). Glycine extracts of the mutant cells demonstrated dramatic changes in protein immunoreactivity by 2D-PAGE with western blotting with HS:2 serotyping sera (FIG. 8b,e). Several of the proteins which showed a change in the mobility and/or immunoreactivity on 2D gels were identified by mass fingerprint analysis (Table I). The protein identifications are in agreement with those identified by SBA lectin affinity chromatography, providing further evidence that the proteins reactive with the GalNAc lectin are glycosylated by the Pgl pathway. The full set of SBA-reactive proteins was not observed in this experiment since it was performed on whole glycine extracts and at different pH range, ie FIGS. 4 and 8 are not directly comparable. In addition, PEB3 was purified from the pglB mutant by ion-exchange chromatography as described above, and analysis by mass spectrometry showed that the protein completely lacked the glycan (FIG. 2c,d).

To show that the pglB mutation only affected the glycosylation of the glycoproteins, analyses were performed of the lipooligosaccharide and capsular polysaccharide of the mutant. Deoxycholate-PAGE of proteinase K digests and mass spectrometry showed that the mass of the mutant LOS core was identical to that of the wildtype (results not shown). In addition, identical capsular repeats were visible in the extracts of the cells of the wildtype and the isogenic mutant on deoxycholate-PAGE. To further demonstrate that the capsule was unaltered, we examined the polysaccharide by HR-MAS NMR. The spectrum of the mutant was unchanged compared to that of the wildtype (results not shown).

Example 8

Detection of N-linked Glycans in Whole Cells by HR-MAS NMR

Figure 9:
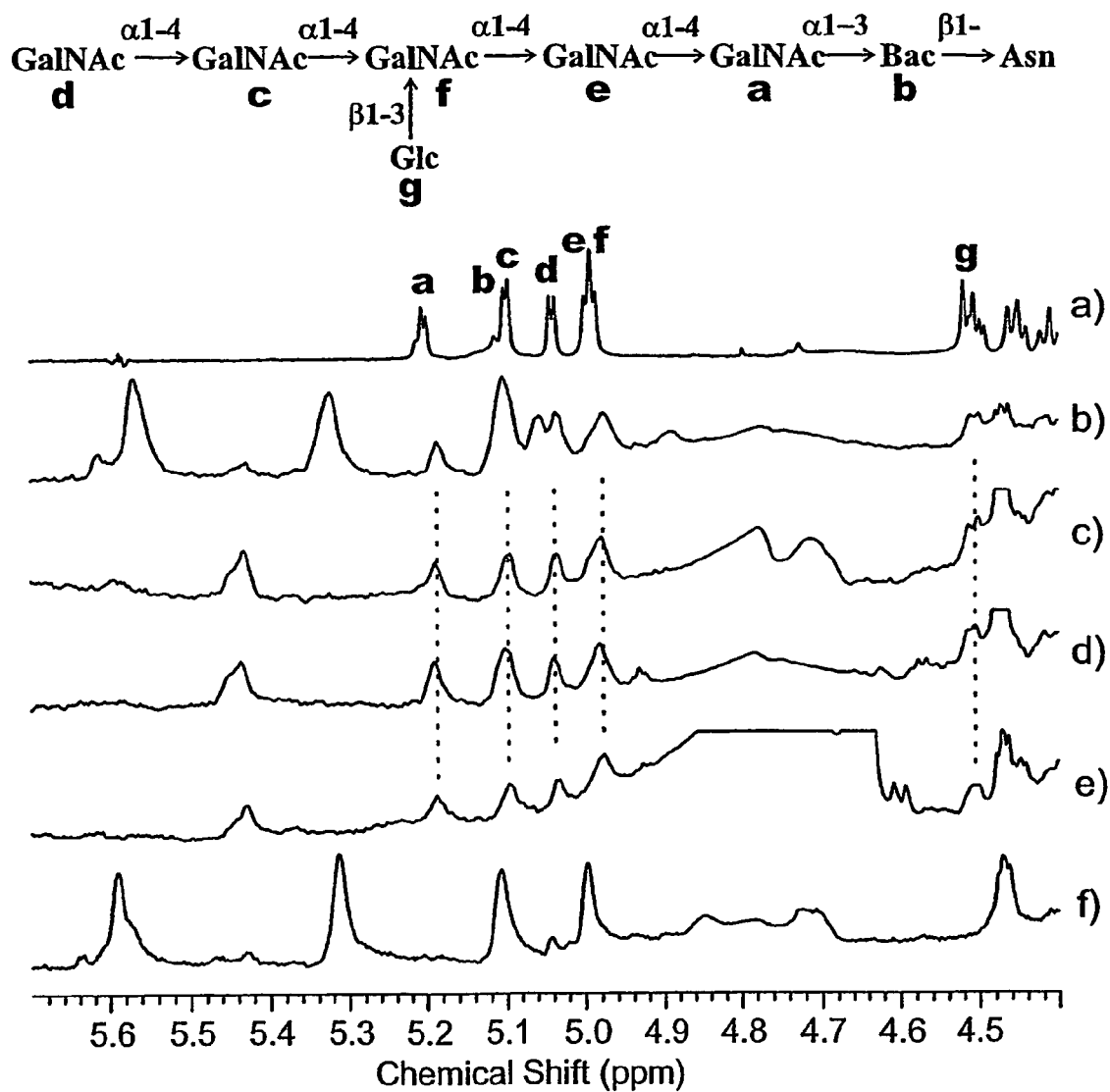
FIG. 9. Detection of the N-linked glycan in the HR-MAS proton NMR spectra from various *campylobacter* strains. The structure of the N-linked glycan is shown above the spectra. a) Spectrum of the purified N-linked glycan in *C. jejuni* NCTC 11168 showing the anomeric resonances labeled a to g. HR-MAS NMR spectra using a 10 ms CPMG filter of whole cells of b) *C. jejuni* NCTC11168, c) *C. jejuni* NCTC11168 kpsM-, d) *C. jejuni* HS:19 serostrain, e) *C. coli* HS:30 serostrain and f) *C. jejuni* NCTC11168 pglB-. Common resonances in b) to e) compared to those in a) are indicated by vertical dotted lines. The HOD resonance at 4.8 ppm was saturated and digitally filtered.

In the HR-MAS NMR spectra of intact *campylobacter* cells (FIG. 9), a set of common $^1$H resonances was detected. We previously determined the structure of the N-linked glycan of *C. jejuni* NCTC 11168 using MS and nano-NMR techniques to be a heptasaccharide (13). As can be observed in the HR-MAS spectra of *C. jejuni* NCTC11168, NCTC11168 kpsM-, *C. jejuni* HS:19 and *C. coli* HS:30, anomeric resonances which matched with those of the purified N-linked glycan were observed, suggesting that this glycan was common to all (FIG. 9). In the spectra of NCTC11168 (FIG. 9b), resonances corresponding to the N-linked glycan were less intense than the resonances from the CPS and some of the anomeric resonances overlapped. However, they could clearly be distinguished when the capsular resonances were eliminated in the NCTC11168 kpsM mutant (FIG. 9c). The assignment of the common glycan resonances to the N-linked glycan could be validated further by examining the spectra of the NCTC11168 pglB mutant in which protein glycosylation has been abolished (3, 13). As expected, the resonances of the N-linked glycan could not be observed in the NMR spectrum of this mutant (FIG. 9f).

Figure 10:
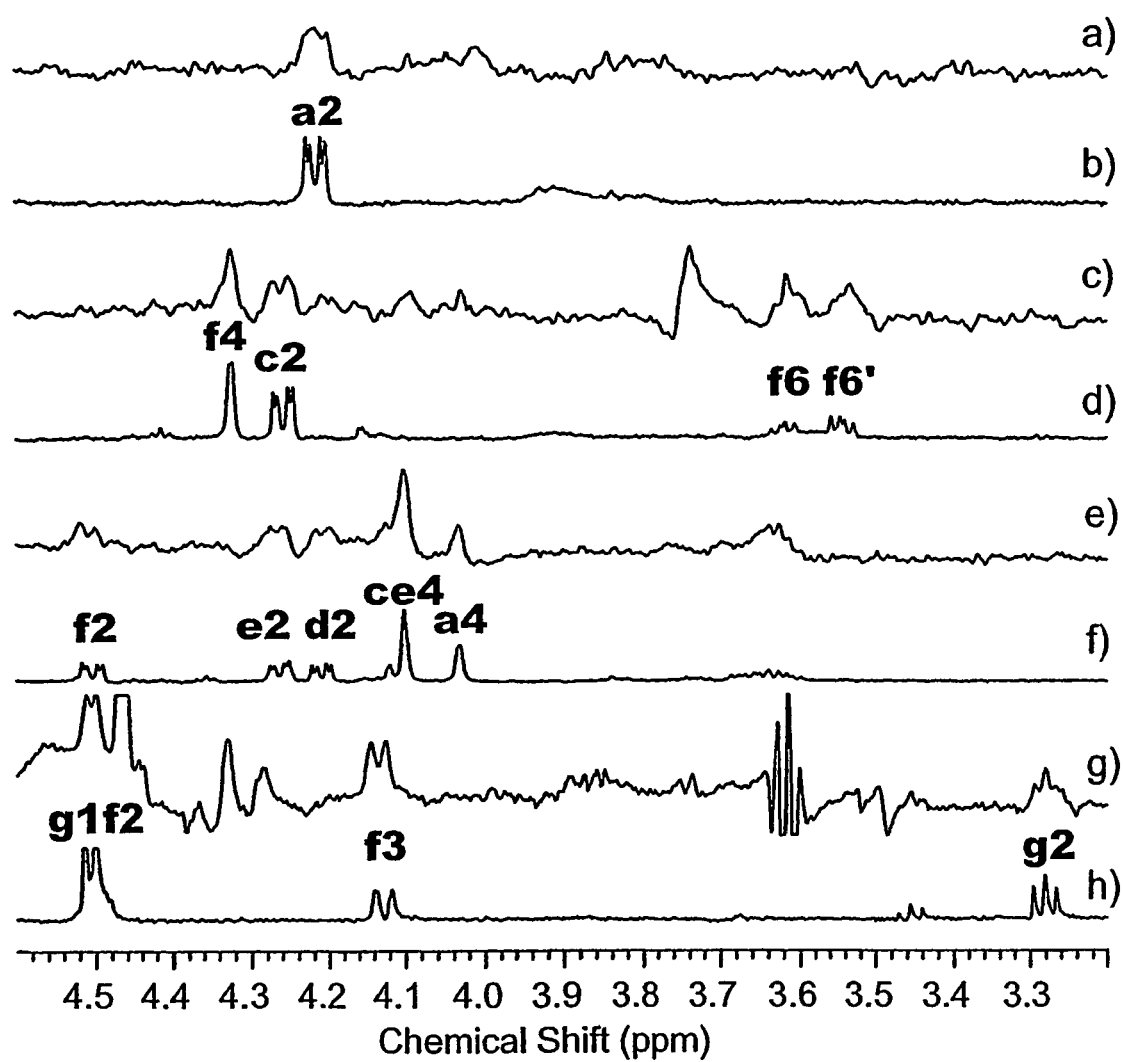
FIG. 10. Comparison of selective NMR experiments of *C. jejuni* HS:19 cells and the purified N-linked glycan. HR-MAS spectra of *C. jejuni* HS:19 (a), c), e), g)) and NMR spectra of the purified N-linked glycan (b), d), f), h)). a) NOESY[a1, 90 Hz, 250 ms]. b) NOESY[a1, 40 Hz, 400 ms]. c) NOESY [b1c1, 60 Hz, 250 ms]. d) NOESY[b1c1, 40 Hz, 400 ms]. e) NOESY[d1e1f1, 90 Hz, 250 ms]. f) Sum of NOESY[d1, 20 Hz, 400 ms] and of NOESY[e1f1, 25 Hz, 400 ms]. g) TOCSY [g1f2, 72 Hz, 47 ms]. h) TOCSY[g1f2, 15 Hz, 33 ms].

The identity of the putative common glycan was further confirmed using selective TOCSY and NOESY experiments (FIG. 10). Experiments were carried out using *C. jejuni* HS:19 cells, since anomeric resonances of the N-linked glycan could be clearly observed. A standard selective NOESY experiment starting with selective irradiation of the a1 resonance in HS:19 established a correlation with a resonance at 4.21 ppm (FIG. 10a). This resonance has the same chemical shift as the a2 resonance observed in the NOESY spectra for the a1 resonance in the purified glycopeptide (FIG. 10b). Comparison of the NOE patterns for other anomeric resonances between HS:19 and the purified N-linked glycan clearly indicated a similar match between the two sets of experiments (FIG. 10c-f). Since the NOE experiments reveal both intra- and inter-residue correlations, this agreement suggests that the sequence of the common glycan is identical to that of the purified N-linked glycan reported previously (13). A selective TOCSY experiment with irradiation of the g1 and f2 overlapping resonances at 4.5 ppm gave rise to cross peaks corresponding to the g2 and f3 resonances (FIG. 10g). Their multiplet shape and chemical shifts matched with those observed in the corresponding experiment for the purified N-linked glycan (FIG. 10h). Other resonances observed were due to partial excitation of the stronger CPS resonances. Hence, the selective excitation experiments performed on the bacterial cells established the in situ identity of the common N-linked glycan.

Figure 11:
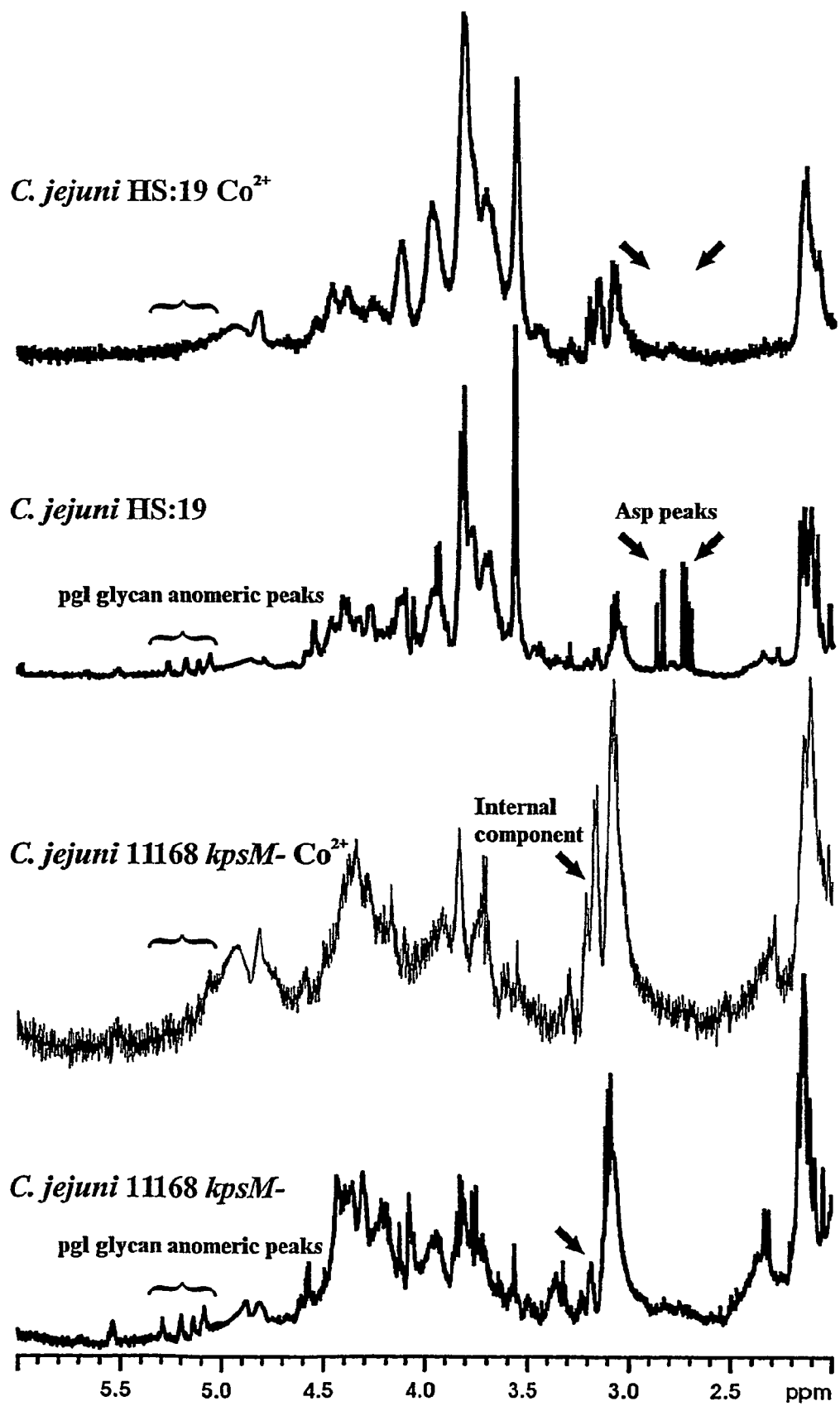
FIG. 11. The spectrum of the purified N-linked glycan in *C. jejuni* NCTC11168 showing the anomeric resonances labeled a to g with common resonances indicated by vertical dotted lines is shown for comparison.

Detection of the N-linked glycan in the HR-MAS proton NMR spectra from various *Campylobacter* species is shown in FIG. 11. The structure of the N-linked glycan is shown above the spectra. The spectrum of the purified N-linked glycan in *C. jejuni* NCTC11168 showing the anomeric resonances labeled a to g with common resonances indicated by vertical dotted lines is shown for comparison. HR-MAS NMR spectra using a 10 ms CPMG filter of whole cells of *C. coli* HS:30 (NCTC 12532, isolated from a pig in Brussels), *C. coli* 423 (isolated from a chicken in Alberta) and *C. fetus* ssp. *venerealis* Biotype A (NCTC 10354 isolated from the vaginal mucus of a cow) are shown. The HOD resonance at 4.8 ppm was saturated and digitally filtered.

Figure 12:
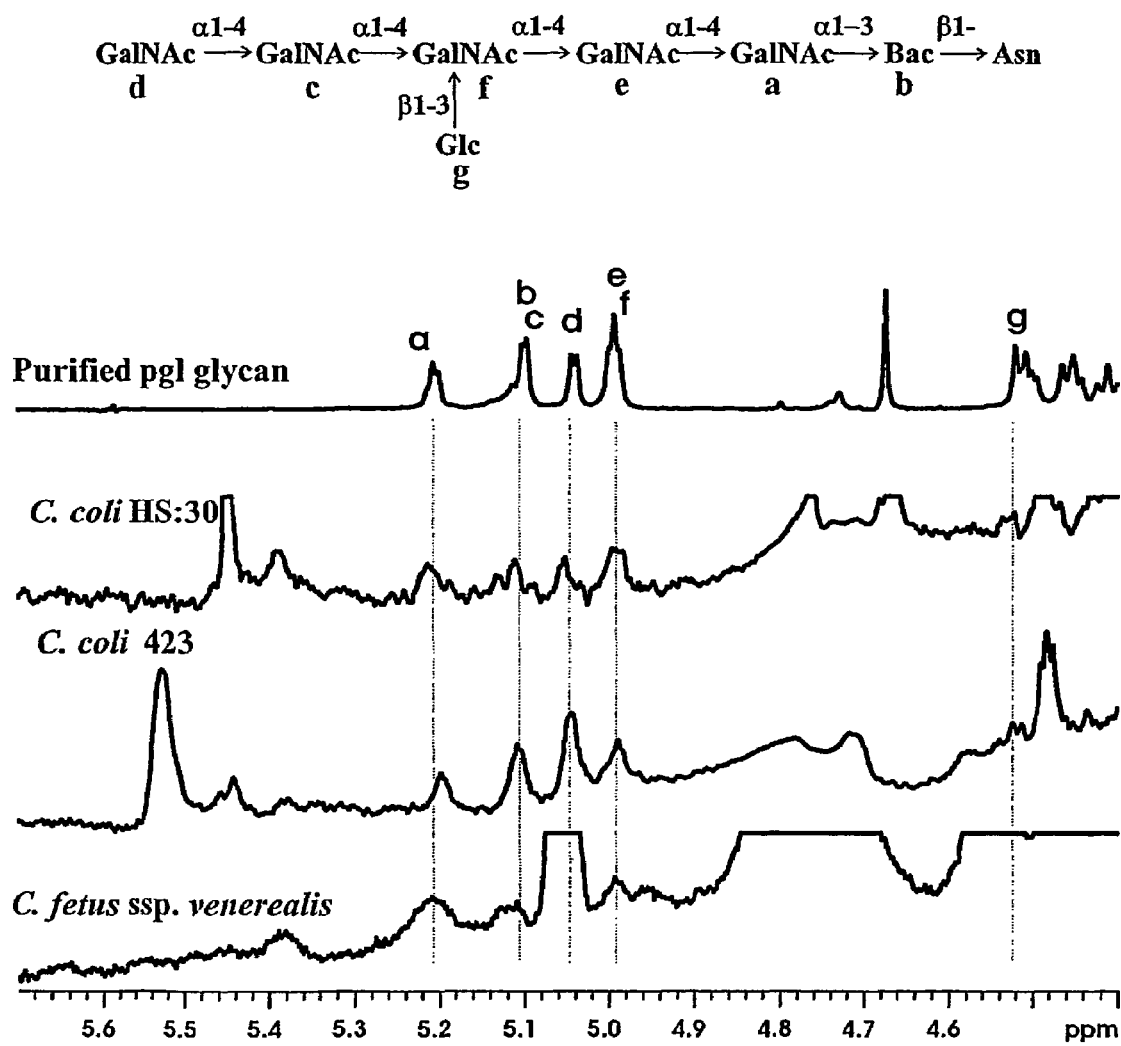
FIG. 12. High resolution magic angle spinning NMR with and without cobalt chloride to demonstrate surface exposure of the N-linked Pgl glycan.

FIG. 12 shows high resolution magic angle spinning NMR with and without cobalt chloride to demonstrate surface exposure of the N-linked Pgl glycan. The top spectrum in each is from samples in which $CoCl_2$ is added. They have been processed identically. Note that the signal to noise ratio (S/N) of the top spectrum is much less than that of the bottom spectrum in each. Since the spectra are acquired with effectively a T2 filter, therefore lines that have been broadened by the $CoCl_2$ will appear weaker. Note that for the kspM mutant, peaks near 3.15 ppm exhibit very different relative intensities to the peak(s) near 3 ppm. The absolute S/N for the peaks near 3.15 ppm with/without $CoCl_2$ is approximately the same while that for the peak that at 3 ppm is very different. This indicates that the peaks at 3.15 ppm are most likely internal and not available to $CoCl_2$. Thus external residues are significantly reduced in intensity. In the case of HS:19, the same observation can be made for the 3.15 ppm versus 3 ppm peaks. Additionally, the aspartic acid peaks at ~2.7 and ~2.85 ppm (see Szymanski et al, JBC, 2003) disappear in the present of $CoCl_2$ which confirms that residues exposed on the external surface or to the medium are broadened. Since the N-linked Pgl glycan resonances (see Szymanski et al, JBC, 2003 and FIG. 9) essentially disappear in the present of $CoCl_2$, this indicates that they too are on the cell surface.

Preparation and Administration of Antibodies and Vaccines

Antibodies or antigen-binding fragments thereof that specifically bind to the glycan moiety according to the invention may be produced by conventional methods. For example, murine monoclonal antibodies may be raised against the glycan of Formula I (including fragments) optionally linked to an oligopeptide or amino acid or immunogenic conjugate. Another strategy is to pan a pre-existing library of cloned genes derived from a camelid lymphocite and capable of expressing dAb antibody fragments, to identify and isolate genes capable of expressing fragments having immunogenic activity against the selected antigen. The gene(s) thus isolated may be are expressed in a bacteriophage library which has been modified to contain this gene. Such an antigen may comprise the heptasaccharide described above or a fragment of such a heptasaccharide, optionally linked as described above to an amino acid, oligopeptide or other conjugate. This method is described in U.S. Pat. No. 5,759,808 to Casterman et al. A still further strategy is to incorporate the gene for expressing the selected antibody or fragment into the genome of a suitable plant which may then serve as a livestock food source. Such a plant would then express the antibody or antibody fragment and when consumed by livestock would thus deliver a suitable dose of the antibody or fragment to the animal.

It will thus be seen that a variety of methods exist to generate antibodies or fragments which specifically bind the glycans of the present invention. Such antibody fragments may be prepared or produced independently of a complete antibody.

Antibodies may also be prepared by the traditional means of isolation of such antibodies from serum of an animal which has been administered suitable doses of the antigen identified in the above examples. For example such methods are described in U.S. Pat. No. 5,759,808 to Casterman et al. This reference describes use of *Camelid* species to produce a unique type of antibody that does not contain light chains.

Antibodies or fragments as described above may be administered with a suitable carrier to humans or livestock as form of passive immunization. When administered to livestock such as poultry the preferred approach is to provide the antibodies or fragments with feed or drinking water, whether by mixing in a concentrate or supplying a plant product which is modified to express the antibody or antibody fragment. The antibodies or fragments when provided separately may be supplied with suitable carriers as a concentrate for mixing with the feed or drink prior to use.

Such antibodies or fragments administered to livestock combat the presence of *campylobacter* in the livestock, thus preventing the livestock from spreading the pathogens to humans who eat or handle the animal products, as well as protection of groundwater from contamination by animal wastes as described above.

These antibodies and fragments may also be used to diagnose the presence of *campylobacter* bacteria in humans or animals by conventional means. As well, they may also be used as a component of an assay to determine to presence of *campylobacter* in a sample such as water, soil or manure.

The heptasaccharide or fragments, optionally linked to an amino acid, oligopeptide or other suitable conjugate, may also be combined with suitable adjuvants and immunostimulants for administration as a vaccine. For such a purpose, one or more suitable dosages are administered in a conventional manner.

REFERENCES

1. Schäffer, C., Graninger, M., and Messner, P. (2001) *Proteomics.* 1, 248-261.
2. Moens, S. and Vanderleyden, J. (1997) *Arch. Microbiol.* 168, 169-175.
3. Szymanski, C. M., Yao, R., Ewing, C. P., Trust, T. J., and Guerry, P. (1999) *Mol. Microbiol.* 32, 1022-1030.
4. Szymanski, C. M., Burr, D. H., and Guerry, P. (2002) *Infect Immun.* 70, 2242-2244.
5. Thibault, P., Logan, S. M., Kelly, J. F., Brisson, J. R., Ewing, C. P., Trust, T. J., and Guerry, P. (2001) *J. Biol. Chem.* 276, 34862-34870.
6. Parkhill, J., Wren, B. W., Mungall, K., Ketley, J. M., Churcher, C., Basham, D., Chillingworth, T., Davies, R. M., Feltwell, T., Holroyd, S., Jagels, K., Karlyshev, A. V., Moule, S., Pallen, M. J., Penn, C. W., Quail, M. A., Rajandream, M. A., Rutherford, K. M., van Vliet, A. H., Whitehead, S., and Barrell, B. G. (2000) *Nature* 403, 665-668.
7. Pei, Z. H., Ellison, R. T., III, and Blaser, M. J. (1991) *J. Biol. Chem.* 266, 16363-16369.
8. Linton, D., Allan, E., Karlyshev, A. V., Cronshaw, A. D., and Wren, B. W. (2002) *Mol. Microbiol.* 43, 497-508.
9. Wacker, M., Nita-Lazar, M., and Aebi, M. (2001) *Int. J. Med. Microbiol.* 291 Suppl 31, 81.
10. Dell, A. and Morris, H. R. (2001) *Science* 291, 2351-2356.
11. Krinos, C. M., Coyne, M. J., Weinacht, K. G., Tzianabos, A. O., Kasper, D. L., and Comstock, L. E. (2001) *Nature* 414, 555-558.
12. St Michael, F., Szymanski, C. M., Li, J., Chan, K. H., Khieu, N. H., Larocque, S., Wakarchuk, W. W., Brisson, J. R., and Monteiro, M. A. (2002) *Eur. J. Biochem.* 269, 5119-5136.
13. Young, N. M., Brisson, J. R., Kelly, J., Watson, D. C., Tessier, L., Lanthier, P. H., Jarrell, H. C., Cadotte, N., St Michael, F., Aberg, E., and Szymanski, C. M. (2002) *J. Biol. Chem.* 277, 42530-42539.
14. Gilbert, M., Karwaski, M. F., Bematchez, S., Young, N. M., Taboada, E., Michniewicz, J., Cunningham, A. M., and Wakarchuk, W. W. (2002) *J. Biol. Chem.* 277, 327-337.
15. Gilbert, M., Brisson, J. R., Kawarski, M. F., Michniewicz, J., Cunningham, A. M., Wu, Y., Young, N. M., and Wakarchuk, W. W. (2000) *J. Biol. Chem.* 275, 3896-3906.
16. Karlyshev, A. V., Linton, D., Gregson, N. A., Lastovica, A. J., and Wren, B. W. (2000) *Mol. Microbiol.* 35, 529-541.
17. Penner, J. L. and Hennessy, J. N. (1980) *J. Clin. Microbiol.* 12, 732-737.
18. Bacon, D. J., Szymanski, C. M., Burr, D. H., Silver, R. P., Alm, R. A., and Guerry, P. (2001) *Mol. Microbiol.* 40, 769-777.
19. Moran, A. P., Penner, J. L., and Aspinall, G. O. (2000) in *Campylobacter* (Nachamkin, I. and Blaser, M. J., eds) pp. 241-257, American Society for Microbiology, Washington, D.C.
20. Moran, A. P. and Prendergast, M. M. (2001) *J. Autoimmun.* 16, 241-256.
21. Laemmli, U. K. (1970) *Nature* 227, 680-685.
22. LeGendre, N. and Matsudaira, P. (1988) *Biotechniques* 6, 154-159.
23. Rademaker, G. J., Pergantis, S. A., Blok-Tip, L., Langridge, J. I., Kleen, A., and Thomas-Oates, J. E. (1998) *Anal. Biochem.* 257, 149-160.
24. Gharahdaghi, F., Weinberg, C. R., Meagher, D. A., Imai, B. S., and Mische, S. M. (1999) *Electrophoresis* 20, 601-605.
25. Uhrin, D. and Brisson, J. R. (2000) in *NMR in Microbiology: Theory and Applications* (Barbotin, J. N. and Portais, J. C., eds) pp. 165-210, Horizon Scientific Press, Wymondham, U. K.
26. Uhrin, D. and Barlow, P. N. (1997) *J. Magn. Reson.* 126, 148-155.
27. Kupce, E., Keifer, P. A., and Delepierre, M. (2001) *J. Magn. Reson.* 148, 115-120.
28. Piotto, M., Bourdonneau, M., Furrer, J., Bianco, A., Raya, J., and Elbayed, K. (2001) *J. Magn. Reson.* 149, 114-118.

29. Kupce, E., Schmidt, P., Rance, M., and Wagner, G. (1998) *J. Magn. Reson.* 135, 361-367.
30. Vinogradov, E. V., Holst, O., Thomas-Oates, J. E., Broady, K. W., and Brade, H. (1992) *Eur. J. Biochem.* 210, 491-498.
31. Labigne-Roussel, A., Courcoux, P., and Tompkins, L. (1988) *J. Bacteriol.* 170, 1704-1708.
32. Guerry, P., Yao, R., Alm, R. A., Burr, D. H., and Trust, T. J. (1994) *Methods Enzymol.* 235, 474-481.
33. Ahmed, I. H., Manning, G., Wassenaar, T. M., Cawthraw, S., and Newell, D. G. (2002) *Microbiology* 148, 1203-1212.
34. Meiboom, S. and Gill, D. (1958) *Rev. Sci. Instrum.* 29, 688-691.
35. Brisson, J. R., Sue, S. C., Wu, W. G., McManus, G., Nghia, P. T., and Uhrin, D. (2002) in *NMR spectroscopy of glycoconjugates* (Jimenez-Barbero, J. and Peters, T., eds) pp. 59-93, Wiley-VCH, Weinhem.
36. Jansson, P.-E., Kenne, L., and Widmalm, G. (1989) *Carbohydr. Res.* 188, 169-191.
37. Baumann, H., Tzianabos, A. O., Brisson, J. R., Kasper, D. L., and Jennings, H. J. (1992) *Biochem.* 31, 40814089.
38. Hermansson, K., Perry, M. B., Altman, E., Brisson, J. R., and Garcia, M. M. (1993) *Eur. J. Biochem.* 212, 801-809.
39. Molinaro, A., Evidente, A., Sante, I. N., Lanzetta, R., Lo, C. P., Mancino, A., and Parrilli, M. (2002) *Carbohydr. Res.* 337, 467-471.
40. Schäffer, C., Scherf, T., Christian, R., Kosma, P., Zayni, S., Messner, P., and Sharon, N. (2001) *Eur. J. Biochem.* 268, 857-864.
41. Patel, T., Bruce, J., Merry, A., Bigge, C., Wormald, M., Jaques, A., and Parekh, R. (1993) *Biochemistry* 32, 679-693.

The abbreviations used herein are:
Bac, bacillosamine, 2,4-diacetamido-2,4,6-trideoxy-D-glucopyranose;
capLC-MS/MS, capillary liquid chromatography-tandem mass spectrometry;
CE, capillary electrophoresis;
CPMG, Carr-Purcell-Meiboom-Gill;
CPS, capsular polysaccharide;
COSY, correlated spectroscopy;
DIPSI-2, decoupling in the presence of scalar interactions;
ESI-MS, electrospray ionization mass spectrometry;
GBS, Guillain-Barré Syndrome;
HMBC, heteronuclear multiple-bond correlation;
HMQC, heteronuclear multiple quantum correlation;
HR-MAS, high-resolution magic angle spinning;
LOS, lipooligosaccharides;
LPS, lipopolysaccharide;
MALDI-TOFMS, matrix assisted laser desorption time-of-flight mass spectrometry;
MAS, magic angle spinning;
MLEV-17, Malcolm Levitt's decoupling cycle;
MS-mass spectrometry
MS/MS-tandem mass spectrometry
NOESY, nuclear Overhauser effect spectroscopy;
PVDF, polyvinylidene difluoride;
SBA, soybean agglutinin;
TOCSY, total correlation spectroscopy; and
WURST-2, wideband, uniform rate, and smooth truncation.

TABLE I

Identification of proteins from 2-D gels

| Cj Gene | Annotation | Number of sequons[a] | SBA staining[b] | pglB mutant[c] |
|---|---|---|---|---|
| Cj0114[d] | probable periplasmic protein | 2S, 3T | + | + |
| Cj0143c | periplasmic solute binding protein for ABC transport system | 1S, 1T | + | |
| Cj0147c | thioredoxin (TrxA) | | − | |
| Cj0169 | superoxide dismutase (Fe; SodB) | | − | |
| Cj0175c[e] | putative iron uptake ABC transport system periplasmic iron binding protein | 1S, 2T | + | + |
| Cj0200c[d] | probable periplasmic protein | 1T | + | + |
| Cj0238 | probable integral membrane protein | 5S, 1T | − | |
| Cj0289c[d] | major antigenic peptide (PEB3) | 2S | + | + |
| Cj0332c | nucleoside diphosphate kinase (Ndk) | | − | |
| Cj0334 | alkyl hydroperoxide reductase (AhpC) | | − | |
| Cj0376 | probable periplasmic protein | 1S, 1T | + | |
| Cj0415[e] | putative oxidoreductase sub-unit | 3T | + | |
| Cj0420 | probable periplasmic protein | 1T | ± | + |
| Cj0493 | translation elongation factor EF-G (FusA) | 1T | ± | |
| Cj0511 | probable secreted proteinase | 2S, 2T | + | + |
| Cj0638c | inorganic pyrophosphatase (Ppa) | | − | |
| Cj0694 | probable periplasmic protein | 4S, 2T | + | |
| Cj0715 | transthyretin-like periplasmic protein | | − | + |
| Cj0779 | thioredoxin peroxidase (Tpx) | 1S | + | |
| Cj0835c | aconitate hydratase (AcnB) | 1S, 2T | + | |
| Cj0843c[e] | putative secreted trans-glycosylase | 5S, 3T | + | |
| Cj0906c | probable periplasmic protein | 2S, 2T | + | |
| Cj0944c | probable periplasmic protein | 1S, 1T | + | |
| Cj0998c | probable periplasmic protein | 1S, 1T | + | + |
| Cj1018c | branched-chain amino-acid ABC transport system periplasmic binding protein | 1S, 2T | | + |
| Cj1032 | probable membrane fusion component of efflux system | 2T | + | |
| Cj1181c | translation elongation factor EF-Ts (Tsf) | | − | |
| Cj1214c | hypothetical protein | 1S | ± | |
| Cj1221 | 60 kD chaperonin (Cpn60; GroEL) | 1S, 2T | + | |
| Cj1345c | probable periplasmic protein | 5S, 2T | + | |
| Cj1380 | probable periplasmic protein | 2T | − | |
| Cj1444c[e] | putative capsule polysaccharide export system periplasmic protein (KpsD) | 3S, 2T | + | |

TABLE I-continued

Identification of proteins from 2-D gels

| Cj Gene | Annotation | Number of sequons[a] | SBA staining[b] | pglB mutant[c] |
|---|---|---|---|---|
| Cj1496c | probable periplasmic protein | 1S, 1T | + | + |
| Cj1534c | probable bacterioferritin | | − | |
| Cj1565c | paralysed flagellum protein (PflA) | 5S, 2T | + | |
| Cj1643 | putative periplasmic protein | 3S, 1T | | + |
| Cj1659 | periplasmic protein (P19) | | − | |
| Cj1670c[d] | probable periplasmic protein (CpgA) | 4S, 2T | + | + |

[a] S, Asn-Xaa-Ser sequons; T, Asn-Xaa-Thr sequons.
[b] Reactivity with SBA in Western blots of 2D gels.
[c] Proteins with changed spot position and/or immunoreactivity in 2D gels, in the pglB mutant. Cj1018c & Cj1643 were not isolated by SBA chromatography.
[d] Glycopeptides observed by CapLC-MS/MS.
[e] Identified from 1-D gel.

TABLE II

Chemical shifts (ppm) of the *C. jejuni* Asn-linked glycopeptide. Measured at 600 MHz ($^1$H) in $D_2O$, 35° C. with HOD at 4.67 ppm. External acetone methyl resonance at $d_H$ 2.23 ppm and $d_c$ 31.07 pppm. Error on $d_c$ is ±0.2 ppm and ±0.02 ppm for $d_H$. Seven NAc resonances at $d_H$ 2.07, 2.05, 2.04, 2.03, 2.02, 2.02 and 1.95 ppm. NAc-CH$_3$ $d_c$ at 23.1-23.4 ppm. NAc-CO $d_c$ at 175-176 ppm.

| Residue | C1 H1 | C2 H2 | C3 H3 | C4 H4 | C5 H5 | C6 H6 | H6' |
|---|---|---|---|---|---|---|---|
| (a) a-GalNAc | 98.0 | 50.7 | 68.0 | 77.6 | 72.7 | 62.2 | |
| | 5.21 | 4.21 | 3.83 | 4.02 | 3.83 | 3.93 | 3.90 |
| (b) β-Bac | 79.0 | 54.5 | 76.3 | 58.1 | 75.0 | 17.6 | |
| | 5.11 | 3.91 | 3.91 | 3.80 | 3.59 | 1.14 | |
| (c) a-GalNAc | 98.3 | 51.6 | 67.9 | 77.5 | 71.8 | 60.9 | |
| | 5.10 | 4.26 | 4.14 | 4.10 | 4.46 | 3.71 | 3.62 |
| (d) a-GalNAc | 99.7 | 51.4 | 68.4 | 69.6 | 72.3 | 60.7 | |
| | 5.04 | 4.20 | 4.01 | 4.03 | 4.36 | 3.67 | 3.61 |
| (e) a-GalNAc | 99.6 | 51.6 | 67.9 | 77.5 | 72.4 | 60.7 | |
| | 5.00 | 4.25 | 4.12 | 4.09 | 4.35 | 3.67 | 3.61 |
| (f) a-GalNAc | 99.9 | 50.7 | 77.5 | 75.8 | 72.5 | 60.5 | |
| | 4.98 | 4.50 | 4.14 | 4.32 | 4.42 | 3.61 | 3.53 |
| (g) β-Glc | 106.1 | 74.1 | 76.9 | 71.1 | 77.2 | 62.1 | |
| | 4.51 | 3.28 | 3.46 | 3.35 | 3.39 | 3.89 | 3.68 |

We claim:

1. An isolated and purified heptasaccharide of formula GalNAc-a1,4-GalNAc-a1,4-[Glc-β1,3]GalNAc-a1,4-GalNAc-a1,4-GalNAc-a1,3-Bac, wherein Bac is 2,4-diacetamido-2,4,6-trideoxy-D-gluco-pyranose.

2. The isolated and purified heptasaccharide as defined in claim 1 obtained from a glycoprotein that is isolated and purified from *Campylobacter jejuni* or *Campylobacter coli*.

3. A pharmaceutical composition comprising the isolated and purified heptasaccharide of claim 1 and a physiologically acceptable carrier.

4. An immunogenic conjugate comprising the isolated and purified heptasaccharide of claim 1.

5. A pharmaceutical composition comprising the immunogenic conjugate as defined in claim 4 and a physiologically acceptable carrier.

6. The pharmaceutical composition as defined in claim 5, further comprising an immunostimulant.

7. An isolated and purified compound that is a heptasaccharide of formula GalNAc-a1,4-GalNAc-a1,4-[Glc-β1,3] GalNAc-a1,4-GalNAc-a1,4-GalNAc-a1,3-Bac, wherein Bac is 2,4-diacetamido-2,4,6-trideoxy-D-gluco-pyranose linked to one amino acid or an oligopeptide.

8. The compound as de fined in claim 7, wherein the heptasaccharide is linked to one amino acid.

9. The compound as defined in claim 7, wherein, said one amino acid is asparagine.

10. The compound—as donned in claim 7 obtained from a glycoprotein that is isolated and purified from a bacterium selected from *Campylobacter jejuni* and *Campylobacter coli*.

11. A pharmaceutical composition comprising the compound as defined in claim 7 and a physiologically acceptable carrier.

12. An immunogenic conjugate comprising, the compound of claim 7.

13. A pharmaceutical composition comprising the immunogenic conjugate as defined in claim 12 and a physiologically acceptable carrier.

14. The pharmaceutical composition as defined, in claim 13 further comprising an immunostimulant.

15. A method of detecting the compound of claim 7 in a sample, the method comprising subjecting said sample to high resolution magic angle spinning nuclear magnetic resonance (HR-MAS NMR) spectroscopy.

16. A method. of detecting the compound of claim 10 in a sample, the method comprising subjecting said sample to high resolution magic angle spinning nuclear magnetic resonance (HR-MAS NMR)spectroscopy.

17. A diagnostic kit for detecting the presence of *campylobacter* in animals or humans, said kit comprising the compound. defined in claim 7.

18. A diagnostic kit for detecting the presence of *campylobacter* in animals or humans, said kit comprising the compound defined in claim 10.

* * * * *

UNITED STATES PATENT AND TRADEMARK OFFICE
CERTIFICATE OF CORRECTION

PATENT NO. : 7,598,354 B2  
APPLICATION NO. : 10/523459  
DATED : October 6, 2009  
INVENTOR(S) : Young et al.

Page 1 of 1

It is certified that error appears in the above-identified patent and that said Letters Patent is hereby corrected as shown below:

In the Claims: should read

Claim 8: The compound as defined in claim 7, wherein the heptasaccharide is linked to one amino acid.

Claim 10: The compound as defined in claim 7 obtained from a glycoprotein that is isolated and purified from a bacterium selected from *Campylobacter jejuni* and *Campylobacter coli*.

Claim 12: An immunogenic conjugate comprising the compound of claim 7.

Claim 14: The pharmaceutical composition as defined in claim 13 further comprising an immunostimulant.

Signed and Sealed this

Twenty-second Day of December, 2009

David J. Kappos  
*Director of the United States Patent and Trademark Office*

UNITED STATES PATENT AND TRADEMARK OFFICE
CERTIFICATE OF CORRECTION

PATENT NO. : 7,598,354 B2
APPLICATION NO. : 10/523459
DATED : October 6, 2009
INVENTOR(S) : Young et al.

It is certified that error appears in the above-identified patent and that said Letters Patent is hereby corrected as shown below:

In the Claims:

Column 25, lines 52-53 should read,
    Claim 8: The compound as defined in claim 7, wherein the heptasaccharide is linked to one amino acid.

Column 26, lines 28-30 should read,
    Claim 10: The compound as defined in claim 7 obtained from a glycoprotein that is isolated and purified from a bacterium selected from *Campylobacter jejuni* and *Campylobacter coli*.

Column 26, lines 34-35 should read,
    Claim 12: An immunogenic conjugate comprising the compound of claim 7.

Column 26, lines 39-40 should read,
    Claim 14: The pharmaceutical composition as defined in claim 13 further comprising an immunostimulant.

This certificate supersedes the Certificate of Correction issued December 22, 2009.

Signed and Sealed this

Twelfth Day of January, 2010

David J. Kappos
*Director of the United States Patent and Trademark Office*

UNITED STATES PATENT AND TRADEMARK OFFICE
CERTIFICATE OF CORRECTION

PATENT NO. : 7,598,354 B2
APPLICATION NO. : 10/523459
DATED : October 6, 2009
INVENTOR(S) : Young et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 344 days.

Signed and Sealed this

Twenty-eighth Day of September, 2010

David J. Kappos
*Director of the United States Patent and Trademark Office*